United States Patent
Manthey

(10) Patent No.: US 7,511,286 B2
(45) Date of Patent: Mar. 31, 2009

(54) IMAGE-BASED FLAT PANEL ALIGNMENT

(75) Inventor: Dieter Manthey, Clayton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 426 days.

(21) Appl. No.: 11/341,396

(22) Filed: Jan. 26, 2006

(65) Prior Publication Data
US 2007/0170373 A1     Jul. 26, 2007

(51) Int. Cl.
*G01N 23/00*     (2006.01)
(52) U.S. Cl. ............. 250/491.1; 250/492.1; 250/503.1; 250/505.1; 378/65; 378/87; 382/128
(58) Field of Classification Search ............. 250/491.1, 250/492.1, 503.1, 505.1; 378/65, 87, 98.4; 382/128
See application file for complete search history.

(56) References Cited

U.S. PATENT DOCUMENTS

| | | | | |
|---|---|---|---|---|
| 4,172,979 A | * | 10/1979 | Morrison | 378/65 |
| 4,223,227 A | * | 9/1980 | Horwitz | 378/206 |
| 5,661,775 A | * | 8/1997 | Cramer et al. | 378/206 |
| 6,014,473 A | * | 1/2000 | Hossack et al. | 382/294 |
| 6,158,708 A | * | 12/2000 | Egley et al. | 248/575 |
| 7,060,997 B2 | * | 6/2006 | Norimine et al. | 250/505.1 |
| 7,356,120 B2 | * | 4/2008 | Main et al. | 378/65 |
| 2002/0181660 A1 | * | 12/2002 | Reinstein et al. | 378/205 |
| 2003/0135105 A1 | * | 7/2003 | Jack et al. | 600/410 |
| 2004/0022363 A1 | * | 2/2004 | Ghelmansarai | 378/206 |
| 2004/0207840 A1 | * | 10/2004 | Sharpe et al. | 356/244 |
| 2006/0173294 A1 | * | 8/2006 | Ein-Gal | 600/427 |
| 2006/0215813 A1 | * | 9/2006 | Scherch et al. | 378/65 |
| 2006/0238706 A1 | * | 10/2006 | Berger et al. | 351/206 |
| 2007/0025524 A1 | * | 2/2007 | Yue | 378/205 |
| 2007/0110289 A1 | * | 5/2007 | Fu et al. | 382/128 |

* cited by examiner

*Primary Examiner*—Jack I Berman
*Assistant Examiner*—Michael J Logie

(57) ABSTRACT

Some embodiments include determination of a first misalignment between an imaging device and an axis of a radiation beam emitted from a treatment head, determination of a rotational misalignment between the imaging device and the treatment head within a plane normal to the axis of the radiation beam, acquisition of an image using the imaging device, and modification of the acquired image based on the determined first misalignment and rotational misalignment. Embodiments may further include determination of a second rotational misalignment between the imaging device and the plane normal to the axis of the radiation beam, and modification of the acquired image based on the determined first misalignment, rotational misalignment and second rotational misalignment.

30 Claims, 20 Drawing Sheets

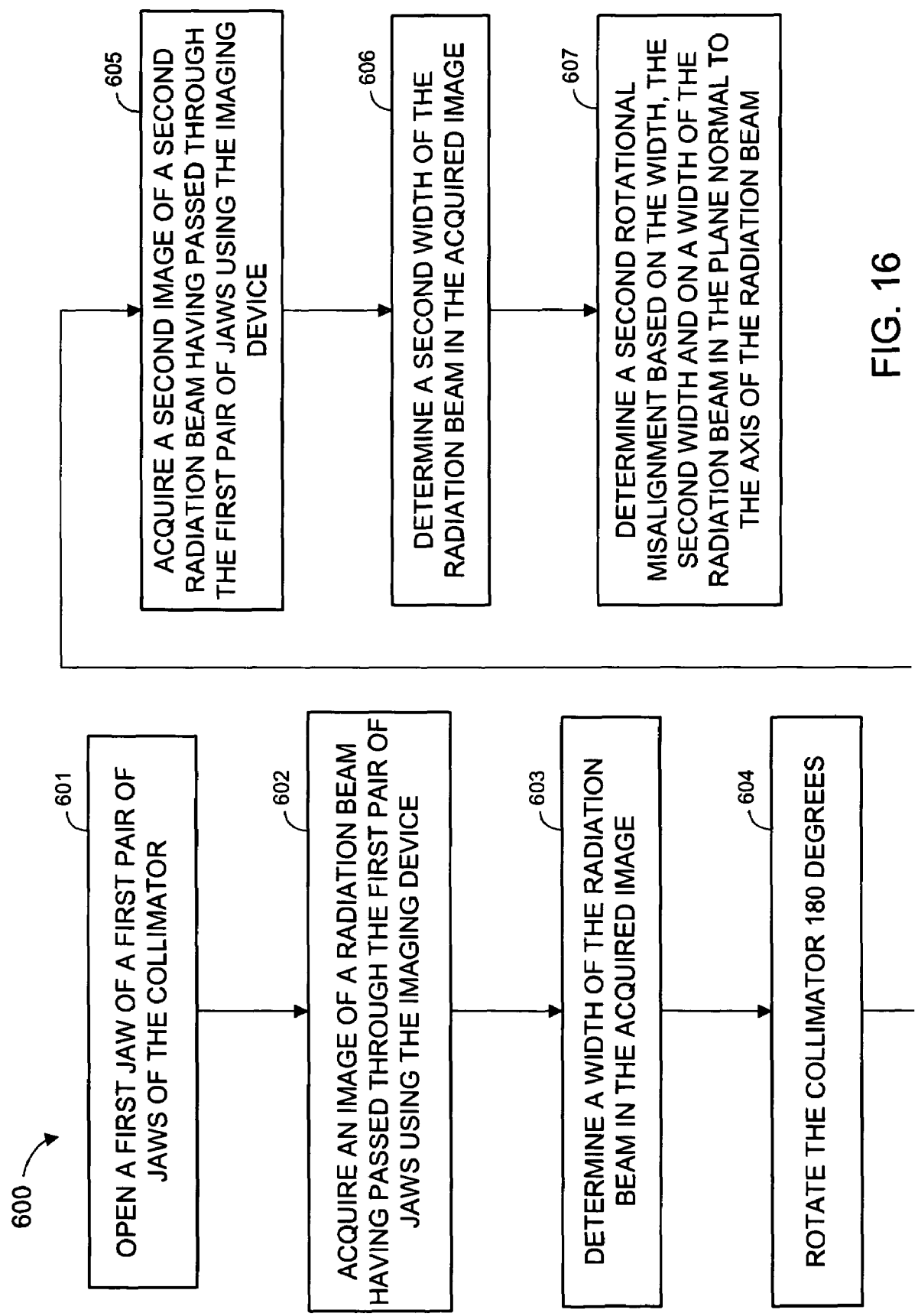

IMAGE-BASED FLAT PANEL ALIGNMENT

BACKGROUND

1. Field

The embodiments described herein relate generally to linear accelerator system. More particularly, the described embodiments relate to geometric calibration of linear accelerator system elements.

2. Description

A linear accelerator produces electrons or photons having particular energies. In one common application, a linear accelerator generates a radiation beam and directs the beam toward a target area of a patient. The beam is intended to destroy cells within the target area by causing ionizations within the cells or other radiation-induced cell damage.

Radiation treatment plans are intended to maximize radiation delivered to a target while minimizing radiation delivered to healthy tissue. To design a radiation treatment plan, a designer must assume that relevant portions of a patient will be in particular positions relative to a linear accelerator during delivery of the treatment radiation. The goals of maximizing target radiation and minimizing healthy tissue radiation may not be achieved if the relevant portions are not positioned in accordance with the treatment plan during delivery of the radiation. More specifically, errors in positioning the patient can cause the delivery of low radiation doses to tumors and high radiation doses to sensitive healthy tissue. The potential for misdelivery increases with increased positioning errors.

Conventional imaging systems may be used to verify patient positioning prior to the delivery of treatment radiation. For example, a low-dose radiation beam is emitted by a linear accelerator prior to treatment, passes through a volume of the patient and is received by an imaging system. The imaging system generates a two-dimensional portal image of the patient volume, which can be used to determine whether the patient is in a position dictated by the particular treatment plan. This determination, however, presumes a particular geometric relationship between the imaging device and the treatment head. Accordingly, the accuracy of the determination depends on whether the imaging system is positioned in accordance with presumed geometric relationship.

Due at least in part to the foregoing, treatment plans are designed under the assumption that positioning errors may occur and may result in misdelivery of radiation. Treatment plans compensate for this potential misdelivery by specifying lower doses and/or using larger beam shapes than would be specified if misdelivery was not expected. Such compensation may decrease as margins of error in patient positioning decrease.

It would therefore be beneficial to provide a system and method that efficiently improves the determination of a patient position with respect to a radiation beam path. When used in conjunction with conventionally-designed treatments, such an improved determination may reduce chances of harming healthy tissue and may allow the use of more aggressive treatments. Specifically, if a margin of error in patient positioning is known to be small, treatment may be designed to safely radiate a greater portion of a tumor with higher doses than in scenarios where the margin of error is larger.

SUMMARY

In order to address the foregoing, some embodiments provide a system, method, apparatus, and means to determine a first misalignment between an imaging device and an axis of a radiation beam emitted from a treatment head, determine a rotational misalignment between the imaging device and the treatment head within a plane normal to the axis of the radiation beam, acquire an image using the imaging device, and modify the acquired image based on the determined first misalignment and rotational misalignment. Embodiments may further include determination of a second rotational misalignment between the imaging device and the plane normal to the axis of the radiation beam, and modification of the acquired image based on the determined first misalignment, rotational misalignment and second rotational misalignment According to some aspects, determination of the first misalignment includes acquisition, using the imaging device, of an image of a reticle mounted to the treatment head, determination of a center of the reticle in the image, determination of a center of the image, and determination of a vector between the center of the image and the center of the reticle in the image. Determination of the rotational misalignment may include determination of a portion of the reticle in the image having a first orientation, and determination of an angle between the portion and a line associated with the first orientation.

Determination of the first misalignment may include, according to some aspects, substantially closing a first pair of jaws of a collimator, acquiring, using the imaging device, an image of a radiation beam having passed through the substantially closed first pair of jaws, rotating the collimator, acquiring, using the imaging device, an image of a second radiation beam having passed through the substantially closed first pair of jaws, determining an intersection point between the image of the first radiation beam and the image of the second radiation beam, determining a center of the image of the first radiation beam or of the image of the second radiation beam, and determining a vector between the center and the intersection point.

Some aspects may also include determination of a second rotational misalignment by opening a first pair of jaws of a collimator, acquiring, using the imaging device, an image of a radiation beam having passed through the first pair of jaws, determining a width of the radiation beam in the acquired image, and determining the second rotational misalignment based on the width and on a width of the radiation beam in the plane normal to the axis of the radiation beam.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein:

FIG. 16 is a flow diagram of process steps pursuant to some embodiments;

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
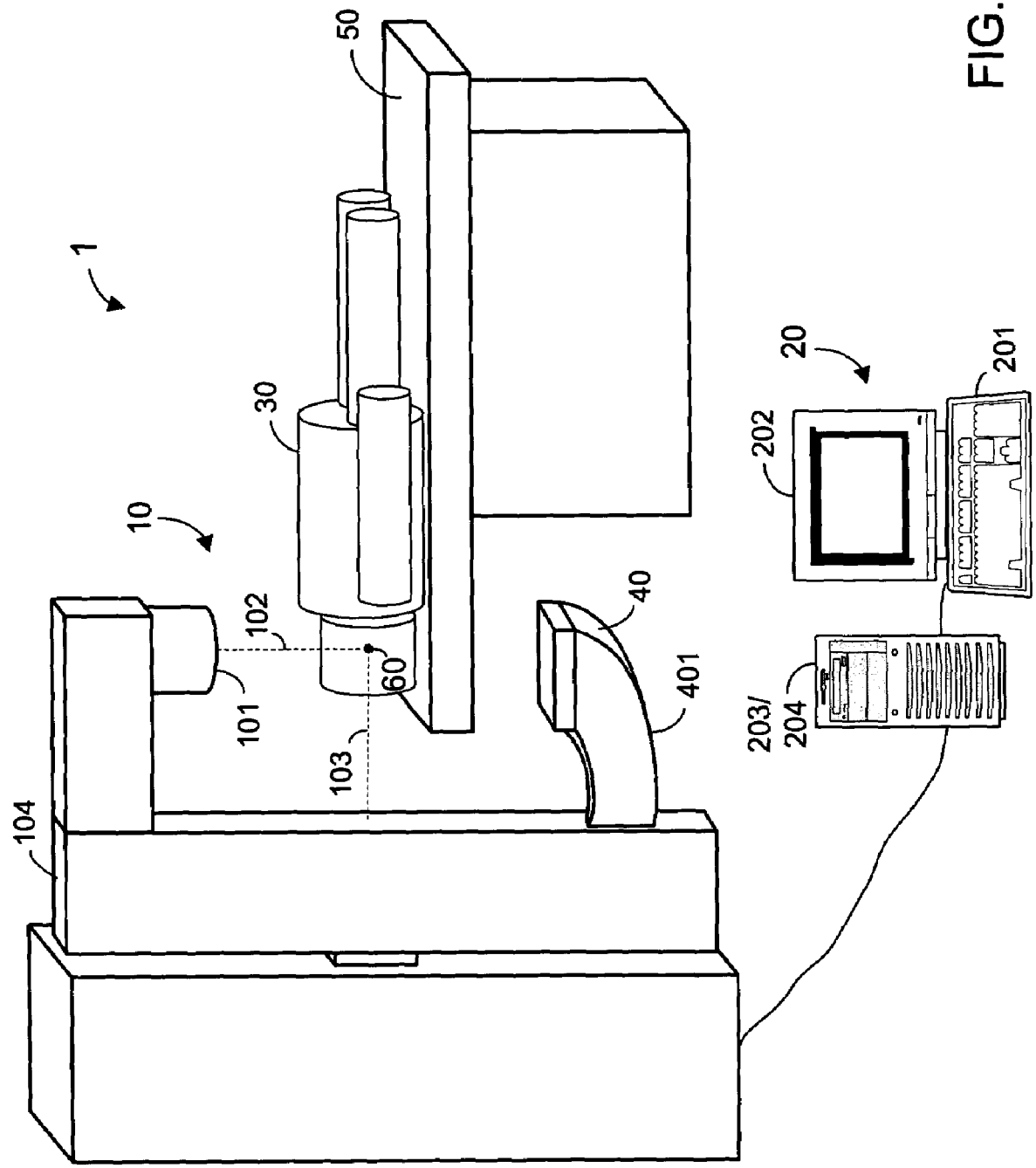
FIG. 1 is a perspective view of a linear accelerator system according to some embodiments.

FIG. 1 is a perspective view of system 1 according to some embodiments. Shown are linear accelerator 10, operator console 20, beam object 30, imaging device 40 and table 50. System 1 may be used to generate radiation for imaging and/or for medical radiation treatment. In this regard, beam object 30 comprises a patient positioned to receive treatment radiation according to a radiation treatment plan. System 1 may be employed in other applications according to some embodiments.

In one example according to some embodiments, elements of console 20 determine a first misalignment between imaging device 40 and an axis of a radiation beam emitted from treatment head 101 of linear accelerator 10, determine a rotational misalignment between imaging device 40 and the radiation beam within a plane normal to the axis of the radiation beam, acquire an image using imaging device 40, and modify the acquired image based on the determined first misalignment and rotational misalignment. The foregoing features may provide efficient determination of a position of object 30 with respect to isocenter 60 of linear accelerator 10.

In this regard, isocenter 60 may be located at an intersection of axis 102 of the aforementioned radiation beam and axis 103 around which gantry 104 is rotatable. Linear accelerator 10 generally delivers a radiation beam from treatment head 101 toward a volume of object 30 that is located at isocenter 60. According to some embodiments, the radiation beam may comprise photon or electron radiation having various energies.

Imaging device 40 may comprise any system to acquire an image based on received photon radiation (i.e., X-rays) and/or electron radiation. Imaging device 40 acquires images that are used before, during and after radiation treatment. For example, imaging device 40 may be used to acquire images for diagnosis, verify and record a patient position, correct a patient position, and verify and record an internal patient portal to which treatment radiation is delivered. As described above, the effectiveness of radiation treatment often depends on the quality of the acquired images.

In some embodiments, imaging device 40 is a flat-panel imaging device using a scintillator layer and solid-state amorphous silicon photodiodes deployed in a two-dimensional array. In other embodiments, imaging device 40 converts X-rays to electrical charge without requiring a scintillator layer. In such imaging devices, X-rays are absorbed directly by an array of amorphous selenium photoconductors. The photoconductors convert the X-rays directly to stored electrical charge that comprises an acquired image of a radiation field. Imaging device 40 may also comprise a CCD or tube-based camera. Such an imaging device may include a light-proof housing within which are disposed a scintillator, a mirror, and a camera.

Imaging device 40 may be attached to gantry 104 in any manner, including via extendible and retractable housing 401. Rotation of gantry 104 may cause treatment head 101 and imaging device 40 to rotate around the isocenter such that the isocenter remains located between treatment head 101 and imaging device 40 during the rotation.

Table 50 supports object 30 during radiation therapy. Table 50 is adjustable to ensure, along with rotation of gantry 104, that a volume of interest is positioned between treatment head 101 and imaging device 40. Table 50 may also be used to support devices used for acquisition of correction images, other calibration tasks and/or beam verification.

Operator console 20 includes input device 201 for receiving instructions from an operator such as an instruction to calibrate system 1 and an instruction to deliver treatment radiation according to a treatment plan. Console 20 also includes output device 202, which may be a monitor for presenting operational parameters of linear accelerator 10 and/or interfaces for controlling elements 10, 40 and/or 50. Output device 202 may also present images acquired by imaging device 40 to determine a misalignment of imaging device 40 or to verify patient positioning prior to radiation treatment. Input device 201 and output device 204 are coupled to processor 203 and storage 204.

Processor 203 executes program code according to some embodiments. The program code may be executable to control system 1 to operate as described herein. The program code may be stored in storage 204, which may comprise one or more storage media of identical or different types, including but not limited to a fixed disk, a floppy disk, a CD-ROM, a DVD-ROM, a Zip™ disk, a magnetic tape, and a signal. Storage 204 may, for example, store radiation treatment plans, portal images, software applications calibrate system 1 and/or to provide radiation treatment, and other data used to perform radiation treatment.

Operator console 20 may be located apart from linear accelerator 10, such as in a different room, in order to protect its operator from radiation. For example, accelerator 10 may be located in a heavily shielded room, such as a concrete vault, which shields the operator from radiation generated by accelerator 10.

Each of the devices shown in FIG. 1 may include less or more elements than those shown. In addition, embodiments are not limited to the devices shown in FIG. 1.

Figure 2:
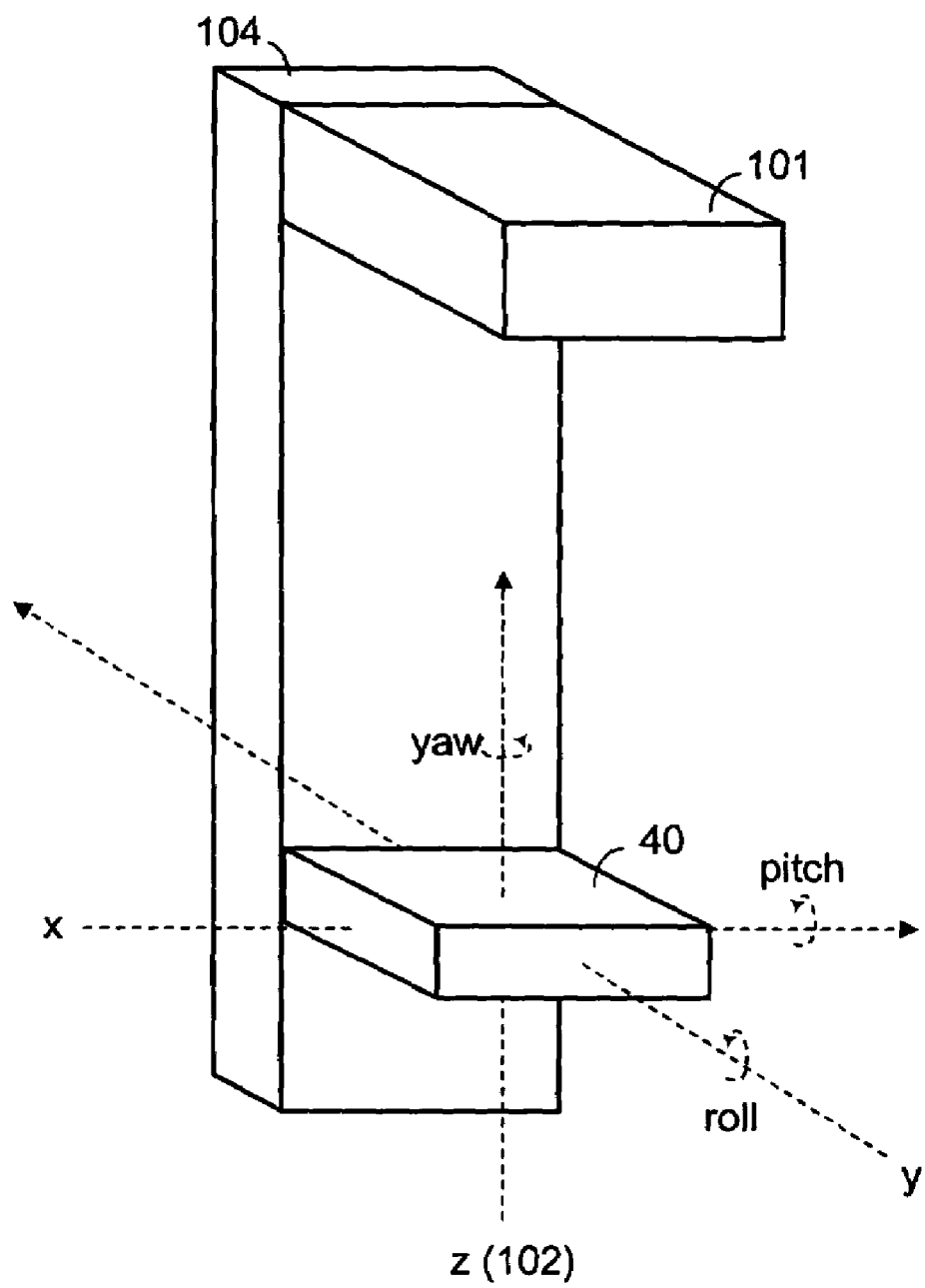
FIG. 2 is a three-dimensional block diagram of a gantry, treatment head and imaging device configuration according to some embodiments.

FIG. 2 is a three-dimensional block diagram to illustrate various ways in which a radiation beam emitted from treatment head 101 and imaging device 40 may be misaligned. For example, a center of imaging device 40 might not intersect axis z (axis 102 of FIG. 1). The center of imaging device 40 according to the present description may be located at the center of an imaging area of imaging device 40 or at any other position at which axis z is presumed to intersect.

Imaging device 40 may also be rotationally misaligned with the radiation beam in a plane normal to axis z and defined by axis x and axis y. In other words, imaging elements of imaging device 40 that are presumed to be oriented in the direction of axis y may be oriented in a direction skew to axis y and imaging elements of imaging device 40 that are presumed to be oriented in the direction of axis x may be oriented in a direction skew to axis x.

Moreover, imaging device 40 may be rotated out of the plane normal to axis z and defined by axis x and axis y. Such a rotation may include one or both of rotation around axis y (roll) and rotation around axis x (pitch). Any of the foregoing misalignments may result in inaccurate determinations of a patient position with respect to a radiation beam path.

Figure 3:
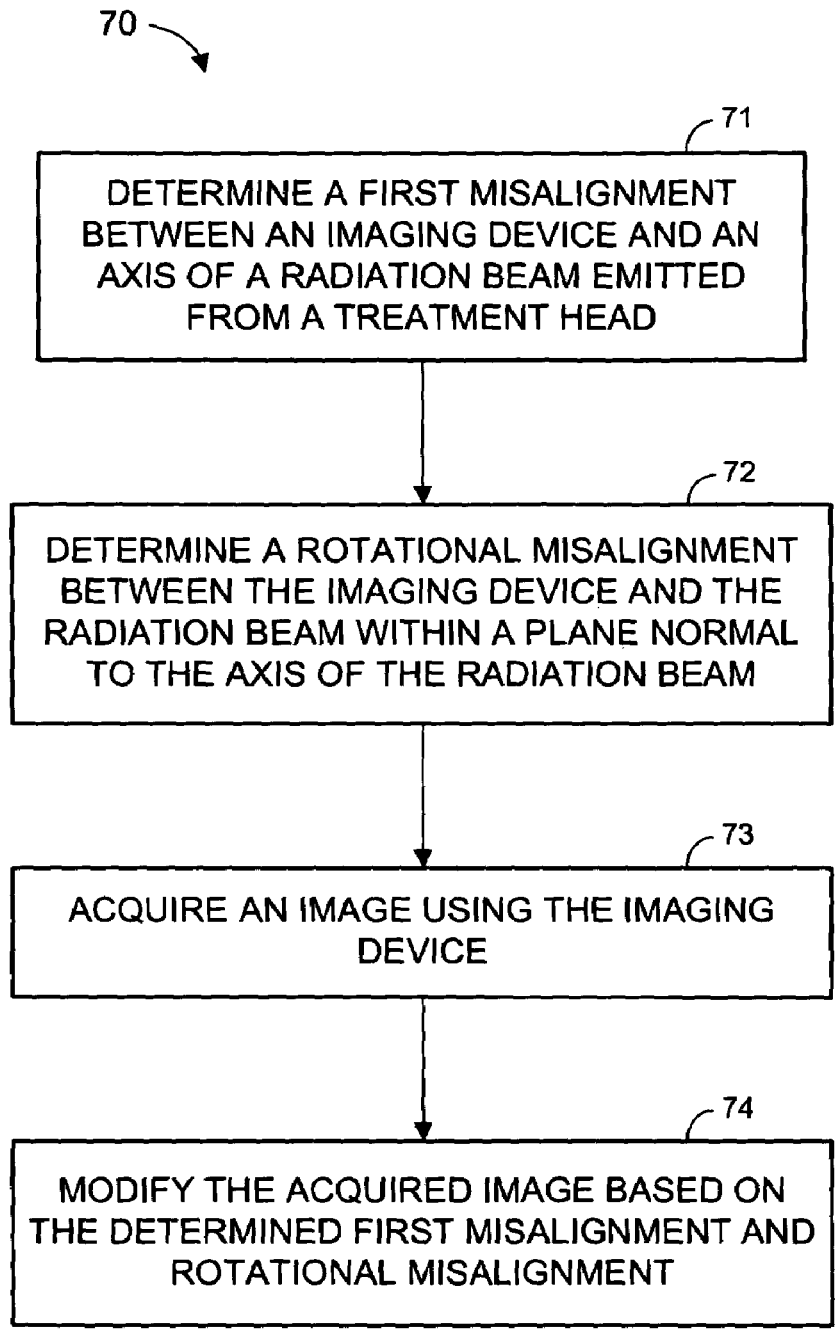
FIG. 3 is a flow diagram of process steps pursuant to some embodiments.

FIG. 3 is a flow diagram of process steps 70 according to some embodiments. Process steps 70 may be executed by one or more elements of linear accelerator 10, operator console 20, treatment head 101, imaging device 40, and other devices. Accordingly, process steps 70 may be embodied in hardware and/or software. Process steps 70 will be described below with respect to the above-described elements, however it will be understood that process steps 70 may be implemented and executed differently than as described below.

Prior to step 71, an operator may use input device 201 of operator console 20 to initiate operation of system 1. In response, processor 203 may execute program code of a system control application stored in storage 204. The operator may then operate input device 201 to initiate a calibration procedure to determine any misalignment of imaging device 40.

At step 71, a first misalignment is determined between an imaging device and an axis of a radiation beam emitted from a treatment head. The first misalignment may correspond to the above-described situation in which axis 102 does not intercept an imaging center of imaging device 40. Some embodiments for determining a first misalignment will be discussed below with respect to FIGS. 6 through 11.

Next, at step 72, a rotational misalignment is determined between the imaging device and the radiation beam within a plane normal to the axis of the radiation beam. The rotational misalignment may comprise any rotation of imaging device 40 from its desired position within the aforementioned x-y plane. Determination of this rotational misalignment according to some embodiments will also be discussed below with respect to FIGS. 6 through 11.

An image is acquired using the imaging device at step 73. The image may comprise a portal image of object 30 prior to delivery of treatment radiation according to a radiation treatment plan. The image may be intended for use in determining whether object 30 is positioned in accordance with the radiation treatment plan.

At step 74, the acquired image is modified based on the determined first misalignment and rotational misalignment. In some embodiments, the image is shifted and rotated at step 74 to compensate for the determined first misalignment and rotational misalignment. Such a modified image may provide an improved determination of a position of object 30 with respect to a radiation beam path.

Digital Imaging Communications in Medicine (DICOM) attributes may be used to modify the acquired image at step 74. For example, the first misalignment may be incorporated into the X-Ray Image Receptor Translation, tag (3002,000D). Moreover, according to some embodiments, the rotational misalignment may be described in the DICOM attribute X-Ray Image Receptor Angle, tag (3002,000E). Specific examples thereof will be provided below.

According to some embodiments, steps 71 and 72 are performed once and several subsequent images acquired by device 40 are modified based on the determined first misalignment and rotational misalignment. Steps 71 and 72 may be repeated periodically (e.g., monthly) to update the determined misalignments.

Figure 4:
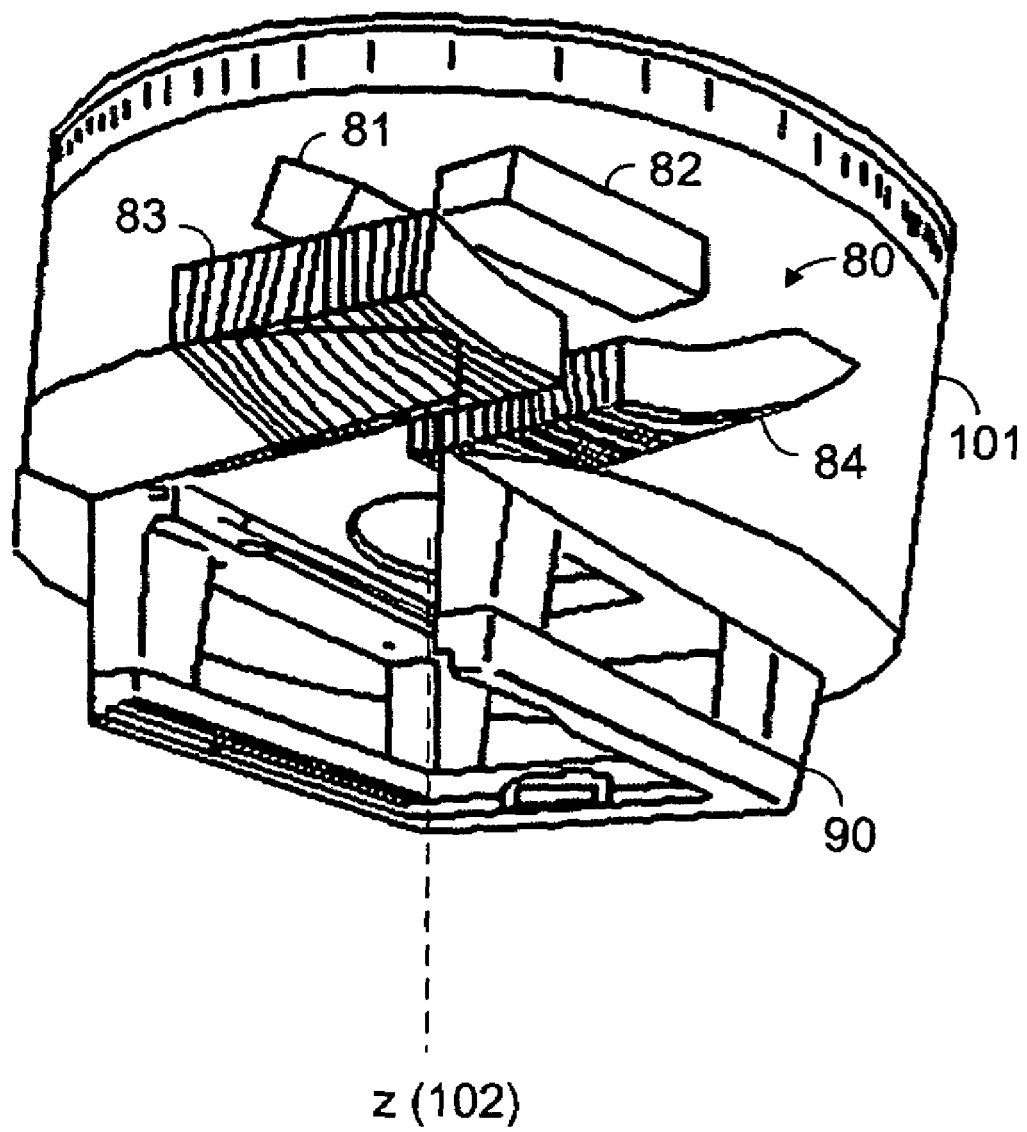
FIG. 4 is a transparent view of a treatment head including a collimator according to some embodiments.
Figure 5:
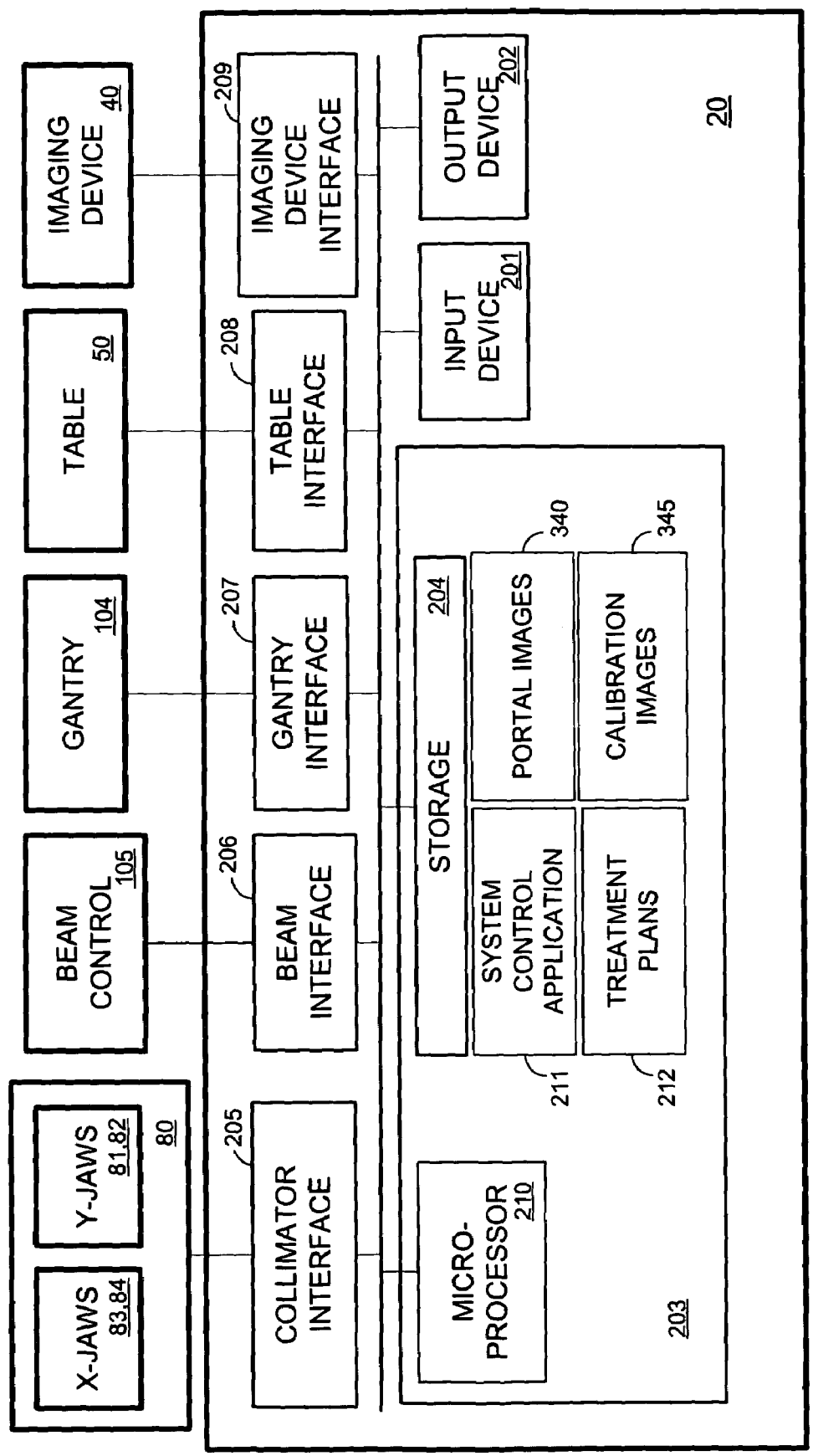
FIG. 5 is a block diagram of a linear accelerator system according to some embodiments.

FIGS. 4 and 5 will now be described to provide additional detail of system 1 that will be referenced in the following operational examples. Embodiments are not limited to the elements and configurations of FIGS. 1, 4 and 5.

FIG. 4 illustrates treatment head 101 according to some embodiments. Treatment head 101 includes collimator 80 that may be used to shape a radiation beam to the dimensions of a tumor. Collimator 80 includes the pair of jaws (Y-jaws) 81 and 82 generally disposed parallel to axis y, and the pair of jaws (X-jaws) 83 and 84 generally disposed parallel to axis x. X-jaws 83 and 84 are located between Y-jaws 81 and 82 and object 30. The positioning of X-jaws 83 and 84 and Y-jaws 81 and 82 determines a size and shape of an opening through which a radiation beam may pass along axis 102.

Each of X-jaws 83 and 84 and Y-jaws 81 and 82 are formed of radiation attenuating material. In one embodiment, the jaws are formed of material that has x-ray transmission characteristics of less than 1%, including but not limited to tungsten.

According to some embodiments, Y-jaws 81 and 82 may be moved toward and away from each other, and X-jaws 83 and 84 may be moved toward and away from each other. Each of X-jaws 83 and 84 and Y-jaws 81 and 82 are controllable to move in an arc toward and away from axis 102. The arc is intended to maintain a correspondence between an edge of each jaw and an edge of the beam edge diverging from its source. Each jaw may move independently of each other jaw according to some embodiments. Also, in some embodiments, X-jaws 83 and 84 and Y-jaws 81 and 82 are independently rotatable about axis 102.

As depicted in FIG. 4, X-jaws 83 and 84 may be formed of a plurality of individual elements. These individual elements may be movable along a path intersecting axis 102. Movement of each element may be individually controllable to generate a wide variety of beam shapes at a tumor.

Treatment head 101 also includes accessory tray 90. Accessory tray 90 may be configured to receive and securely hold attachments used during the course of treatment planning and treatment (such as, for example, reticles, wedges, or the like). According to some embodiments, treatment head 101 is rotatable to rotate collimator 80 and accessory tray 90 around axis 102 without disturbing the maintaining the physical relationships between X-jaws 83 and 84, Y-jaws 81 and 82, and accessory tray 90.

FIG. 5 is a block diagram of elements of system 1 according to some embodiments. As shown, operator console 20 includes several elements for interfacing with other elements of system 1. Specifically, operator console 20 includes collimator interface 205, beam interface 206, gantry interface 207, table interface 208, and imaging device interface 209. Operator console 20 may be implemented by one or more separate computing systems.

Collimator interface 205 may be used to control the opening and closing of each of jaws 81 through 84, the independent rotation of each pair of jaws, and/or the rotation of collimator 80. Beam interface 206 may control beam-generating elements of linear accelerator 10 based on desired beam characteristics. In particular, beam interface 206 may control trigger signals for controlling an injector current and RF power signal to generate a radiation beam having particular radiation energy.

Interfaces 205 through 209 may comprise dedicated hardware and/or software interfaces, and one or more of interfaces 205 through 209 may reside in processor 203. One or more of interfaces 205 through 209 may be implemented by a single interface. For example, interfaces 205 through 207 may be implemented by a single Ethernet interface and interfaces 208 and 209 may be implemented by proprietary interfaces for interfacing with table 50 and imaging device 40.

Processor 203 includes microprocessor 210 and storage 204. Microprocessor 210 may execute processor-executable program code stored in memory 204 to provide some or all of the functionality described herein. In this regard, storage 204 stores processor-executable process steps of system control application 211.

System control application 211 may comprise processor-executable program code to implement process steps 70. System control application 211 may also comprise program code to generate and/or modify a treatment plan according to some embodiments. In this regard, system control application 211 may comprise the COHERENCE™ workspace or the KONRAD™ treatment planning system sold by Siemens Medical Solutions.

Storage may also store treatment plans 212 in accordance with any currently- or hereafter-known format. Treatment plans 212 may comprise scripts that are automatically executable by linear accelerator 10 and treatment table 50 to provide radiation therapy fractions. Each of treatment plans 212 may require a patient to be positioned in a particular manner with respect to treatment head 101.

Storage 204 stores portal images 213 to assist in such positioning. Each of portal images 213 may represent "correct" positioning of a patient for a respective treatment plan. In other words, a portal image 213 may correspond to a treatment plan, and may represent a portal image that should be acquired by imaging device 40 if a patient is correctly positioned for delivery of the treatment plan. Portal images 213 may also include the portal images that are acquired by imaging device 40 and that are subsequently compared to the above-described portal images to determine if the patient is correctly positioned.

Calibration images 214 are images acquired as described herein to determine misalignments between imaging device 40 and a path of a radiation beam emitted from treatment head 101. Calibration images 214 may be discarded after misalignments are determined based thereon. As described herein, portal images 213 that are acquired by imaging device 40 may be modified based on the determined misalignments.

Figure 6:
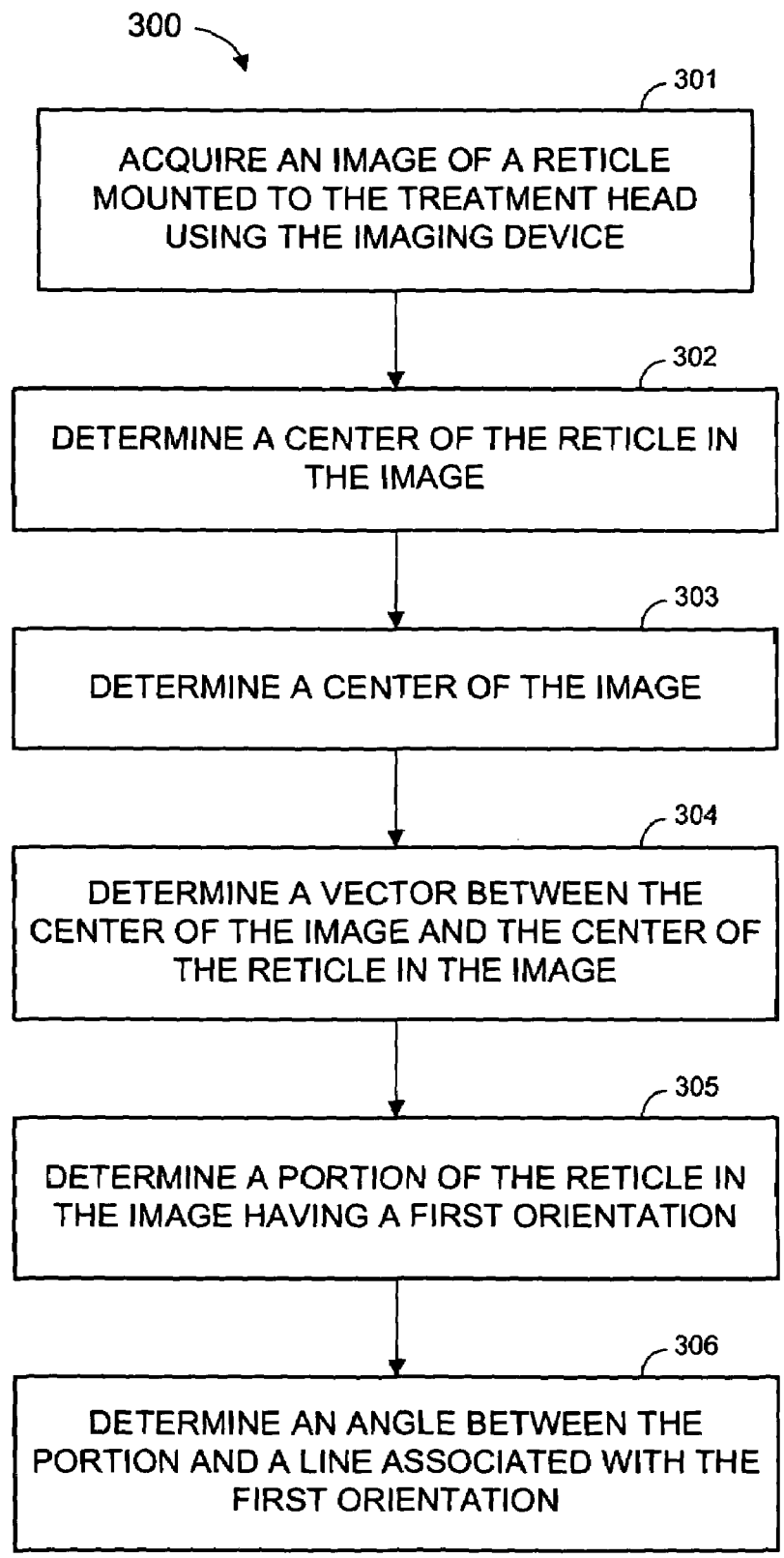
FIG. 6 is a flow diagram of process steps pursuant to some embodiments.

FIG. 6 is a flow diagram of process steps 300 to determine a first misalignment and a rotational misalignment according to some embodiments. Process steps 300 and all other process steps described herein may be executed by one or more elements of linear accelerator 10, operator console 20, treatment head 101, imaging device 40 and other devices. Accordingly, these process steps may be embodied in hardware and/or software and, although described herein with respect to specific elements, may be implemented and executed differently than as described.

An image of a reticle mounted to a treatment head is acquired at step 301. The image is acquired by an imaging device, and the reticle may be mounted to the treatment head in any suitable manner. Step 301 may be initiated at the beginning of a calibration procedure.

The reticle may comprise any device including radiation-attenuating elements that depict a location of axis 102 on the acquired image. These elements may simply comprise two perpendicular wires intersecting at a point where axis 102 intercepts the reticle. In this regard, reticle 102 may be mounted in accessory tray 90 of treatment head 101. The reticle is mounted to treatment head 101 such that the center of the reticle is aligned with axis 102 of linear accelerator 10.

Figure 7:
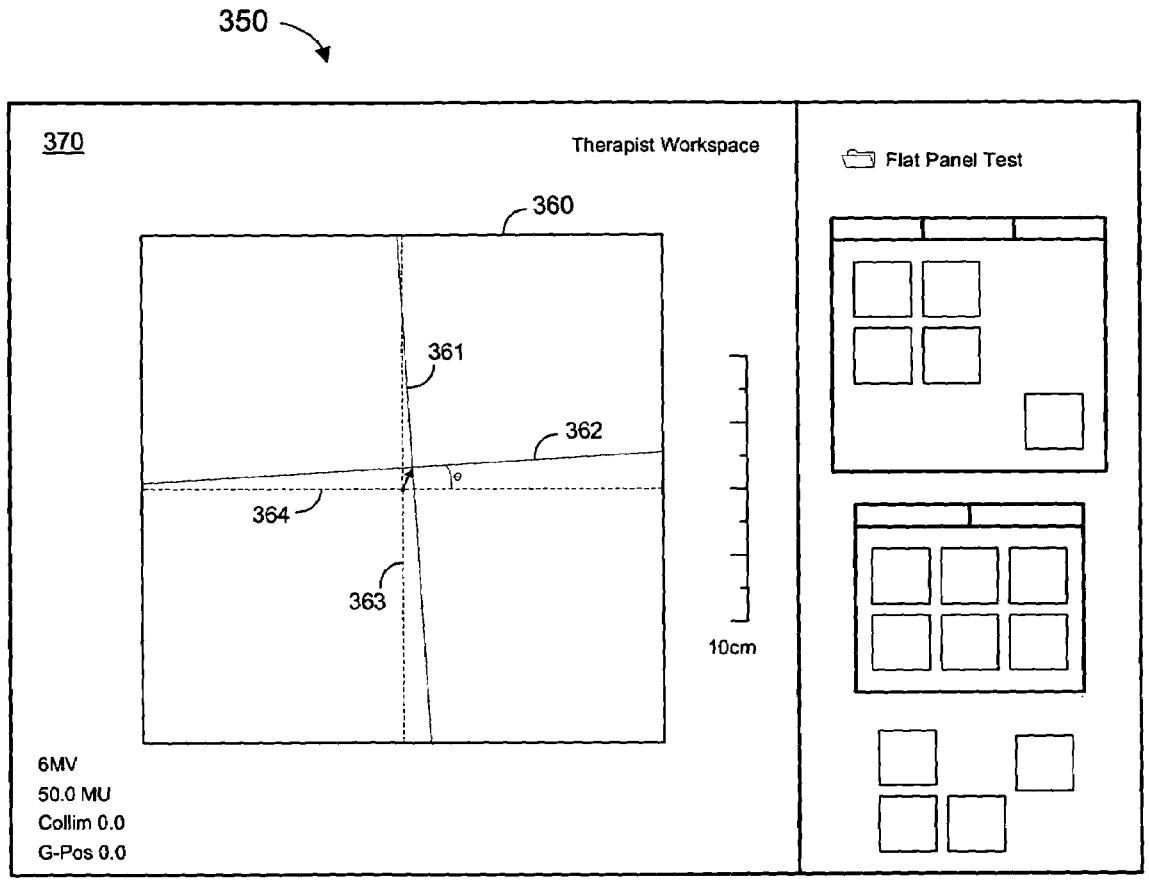
FIG. 7 is a view of a graphical interface of a linear accelerator system according to some embodiments.
Figure 8:
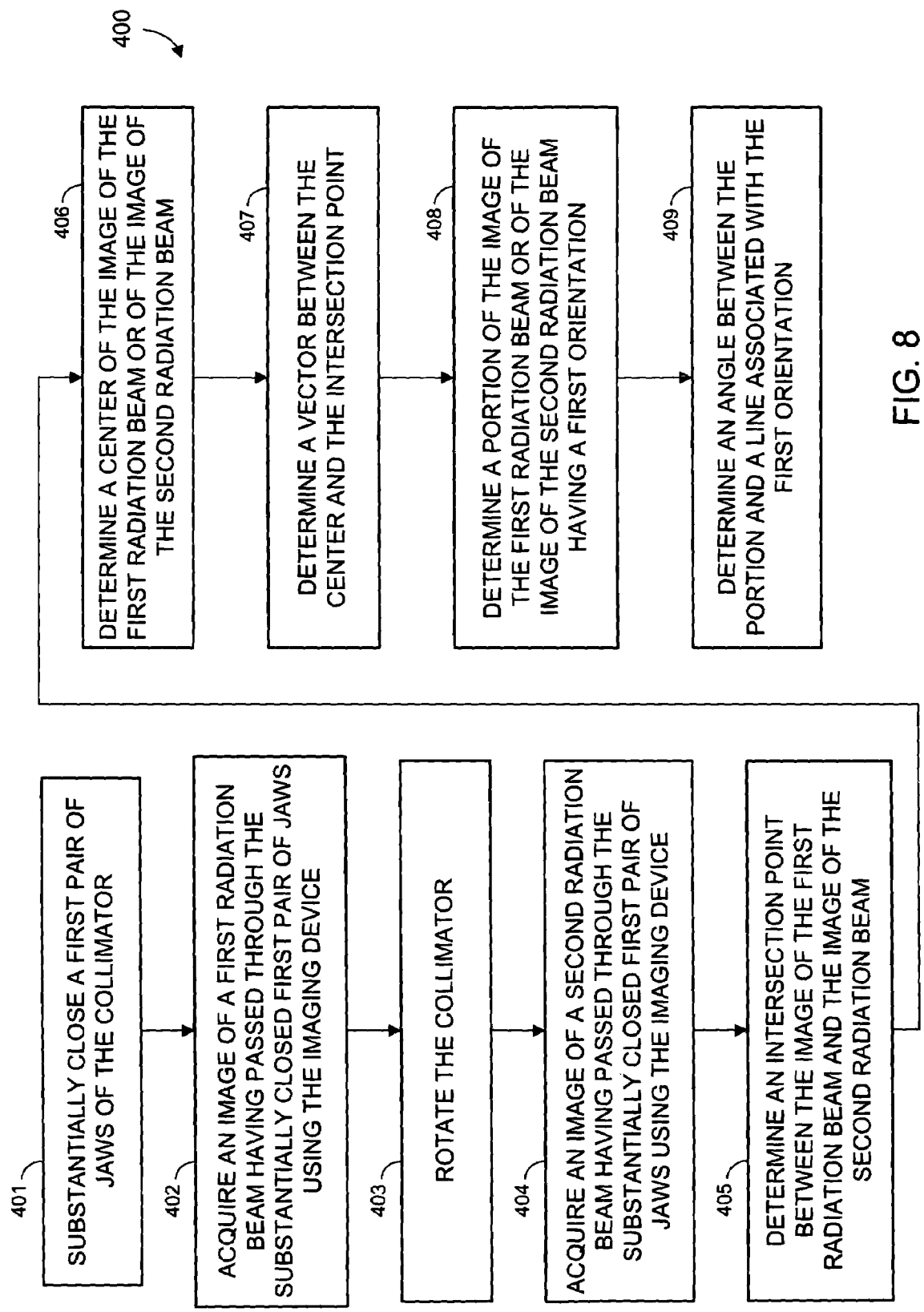
FIG. 8 is a flow diagram of process steps pursuant to some embodiments.

FIG. 7 is an outward view of interface 350 displayed by output device 202 according to some embodiments. Interface 350 may be provided by system control application 211. Interface 350 shows image 360 acquired at step 301 according to some embodiments.

Image 360 is a portion of image 370. Image 370 represents an entire image acquired by imaging device 40, while image 360 comprises a radiation-exposed portion of image 370. Image 360 and other radiation-exposed image portions will be referred to herein as images even though they may comprise portions of larger images as described above.

Image 360 of FIG. 7 may represent the image acquired at step 301 after conventional post-processing is applied thereto. Such post-processing may include one or more of border removal, noise reduction, and identification of two or more points of line 361 and line 362 via threshold detection. Lines 361 and 362 represent radiation-attenuating elements of the reticle as projected onto a plane of imaging device 40.

A center of the reticle in the acquired image is determined at step 302. In the present example, the center of the reticle is located at the point at which the radiation-attenuating elements of the reticle intersect. Other reticles may provide other indicators for determining their centers in the acquired image. As mentioned above, the center of the reticle is aligned with axis 102 of linear accelerator 10. Accordingly, the center of the reticle in image 360 (i.e., the intersection point of line 361 and 362) represents a point at which axis 102 intercepts imaging device 40.

Next, at step 303, a center of the acquired image is determined. The center of the acquired image may simply correspond with the geometric center of image 360. This geometric center might reflect a center of an image-capturing area of imaging device 40, which in turn might not necessarily correspond to a center of the entire structure of imaging device 40 in the plane of the image-capturing area. The center of image 360 is depicted in FIG. 7 as the intersection of dotted lines 363 and 364.

A vector between the center of the image and the center of the reticle in the image is determined at step 304. The vector represents the above-described first (translational) misalignment between axis 102 and a center of an image-capturing area of imaging device 40. The vector according to some embodiments is illustrated as an arrow in image 360 of FIG. 7. Since the vector originates at the origin of a coordinate system having axes 363 and 364, the vector may be represented by the coordinates of the center of the reticle, hereinafter referred to as $(x_d, y_d)$.

At step 305, a portion of the reticle in the image having a first orientation is determined. For example, based on the manner in which the reticle is mounted on treatment head 101, line 362 may be oriented along axis x shown in FIG. 2.

Next, at step 306, an angle is determined between the determined portion and a line associated with the first orientation.

FIG. 7 illustrates such an angle between line 362 and line 364. Line 364 is associated with an orientation along axis x because it is intended to be aligned therewith, even though it is not. Similarly, line 363 is associated with an orientation along axis y because it would be aligned therewith if imaging device 40 were correctly aligned with the radiation beam path. According to some embodiments, the angle may be determined at step 306 by determining [(angle(line 362)–0°)+(angle(line 361)–90°)].

Process steps 400 may also provide determination of the first misalignment and the rotational misalignment according to some embodiments. Process steps 400 do not require a reticle as used in process steps 300.

Initially, a first pair of jaws of a collimator is substantially closed at step 401. The first pair of jaws is substantially closed in order to emit a thin radiation beam from treatment head 101. The thin beam may comprise leakage, is intended to project a thin but definable line onto imaging device 40. According to some embodiments of step 401, collimator interface 205 controls Y-jaws 81 and 82 to close completely. X-jaws 83 and 84 are opened to allow a suitable length of the thusly-shaped beam to be emitted from treatment head 101.

According to some embodiments, X-jaws 83 and 84 are substantially closed at step 401 and Y-jaws 81 and 82 are opened to allow a suitable length of the radiation beam to reach X-jaws 83 and 84. Such an arrangement may be particularly suitable in a case that X-jaws 83 and 84 comprise solid blocks such as Y-jaws 81 and 82 depicted in FIG. 4.

Figure 9:
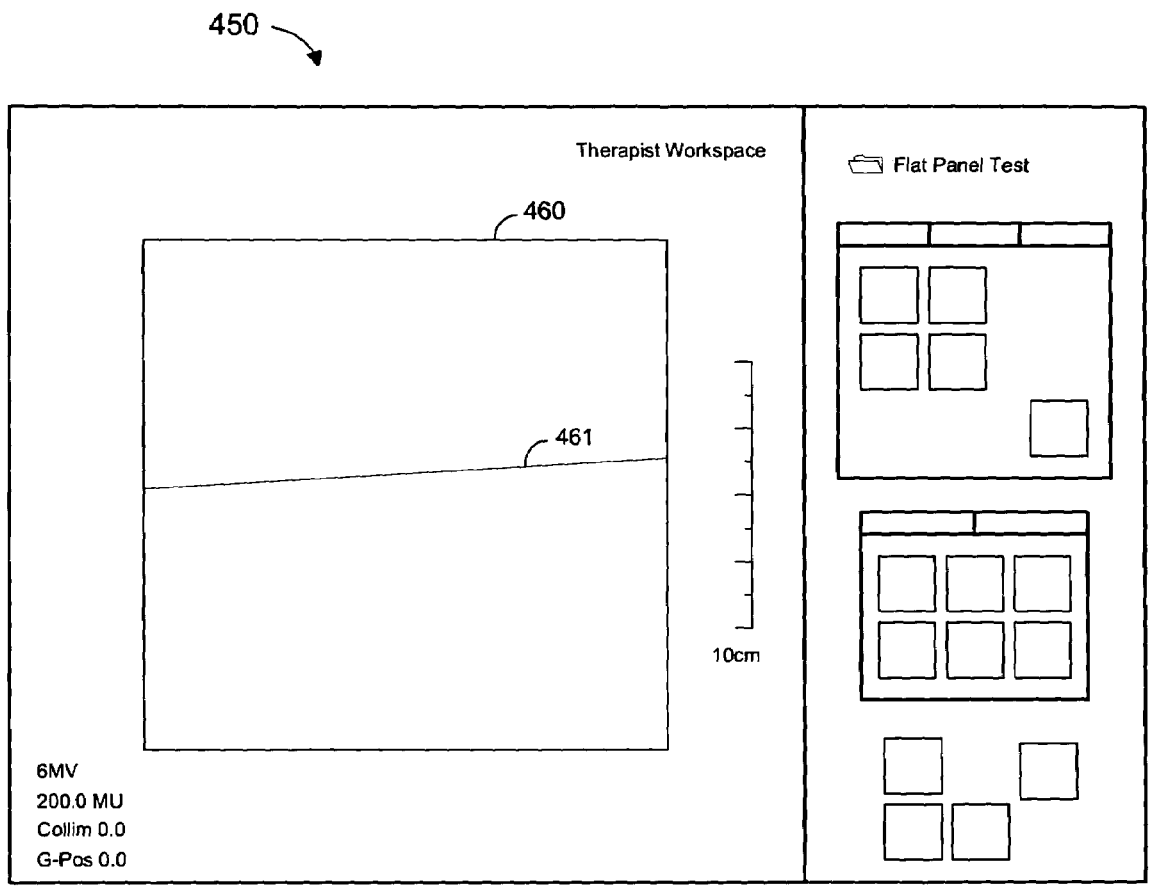
FIG. 9 is a view of a graphical interface of a linear accelerator system according to some embodiments.

An image of a radiation beam having passed through the substantially-closed first pair of jaws is acquired using an imaging device at step 402. FIG. 9 illustrates interface 450 presenting image 460 acquired according to some embodiments of step 402. Line 461 of image 460 represents a radiation beam having passed through substantially-closed Y-jaws 81 and 82 as projected onto an image-capturing area of imaging device 40. Image 460, as well as the other acquired images described herein, may reflect the above-described conventional post-processing in order to provide a sharp representation of line 461 and few artifacts.

Interface 450 indicates that a 6MV radiation beam providing 200MU was used to acquire image 460. The significant dosage is used because most of the radiation beam is blocked by the closed pair of jaws. Interface 450 also indicates that collimator 80 was in its respective "home" position during acquisition of image 460. According to some embodiments, the home position of gantry 104 is shown in FIGS. 1 and 2, and the home position of collimator 80 positions Y-jaws 81 and 82 perpendicular to axis y (i.e., Y-jaws 81 and 82 are movable along axis y), and X-jaws 83 and 84 perpendicular to axis x (i.e., X-jaws 83 and 84 are movable along axis x). As a result of this configuration, line 461 generally follows axis x in image 460, with any deviation therefrom resulting from one or more of the above-described misalignments.

The collimator is then rotated at step 403. Collimator interface 205 rotates collimator 80 by 90° according to some embodiments of step 403. By virtue of this rotation, Y-jaws 81 and 82 become perpendicular to axis x (i.e., Y-jaws 81 and 82 are movable along axis x), and X-jaws 83 and 84 perpendicular to axis y (i.e., X-jaws 83 and 84 are movable along axis y). Collimator 80 may be rotated through any suitable arc according to some embodiments.

Figure 10:
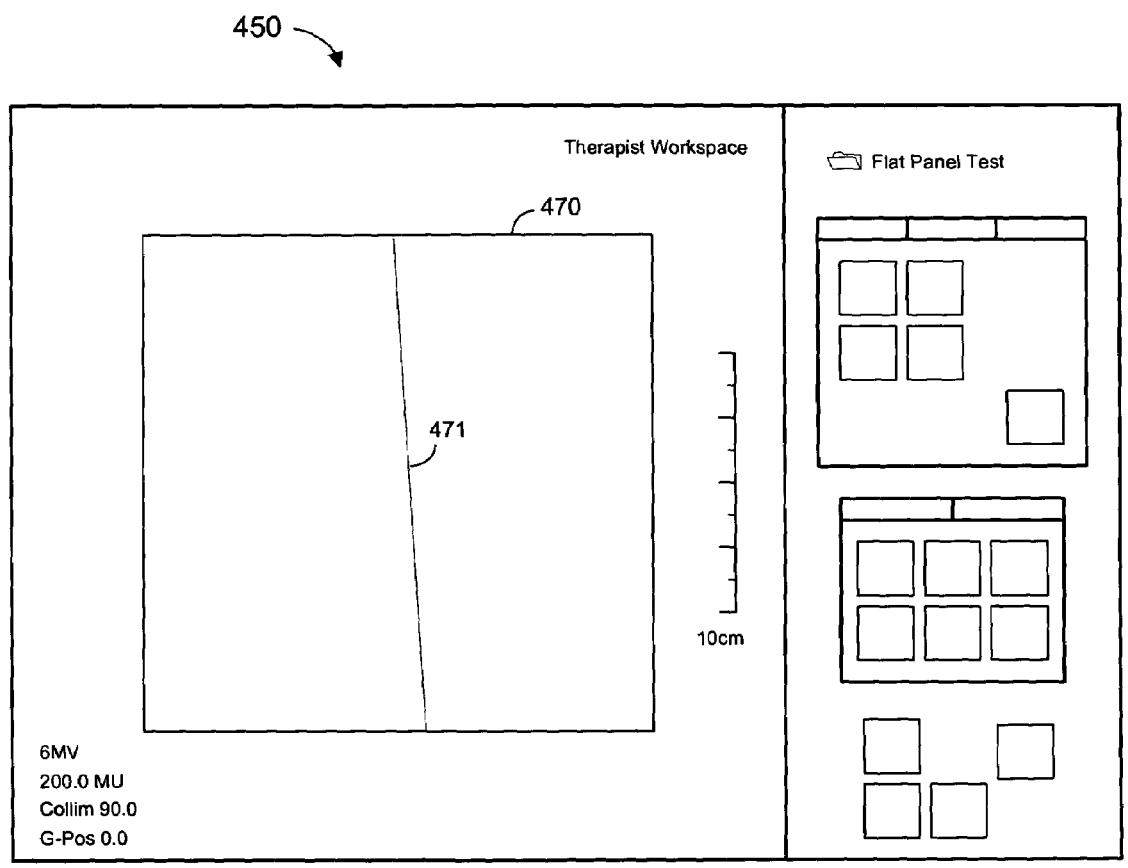
FIG. 10 is a view of a graphical interface of a linear accelerator system according to some embodiments.

An image of a second radiation beam having passed through the substantially-closed first pair of jaws is acquired using an imaging device at step 404. Interface 450 of FIG. 10 presents image 470 as acquired according to some embodiments of step 404. Line 471 of image 470 represents a radiation beam having passed through substantially-closed Y-jaws 81 and 82. Line 471 generally follows axis y because of the rotation of collimator 80 at step 403, with any deviation therefrom again resulting from one or more of the above-described misalignments.

Figure 11:
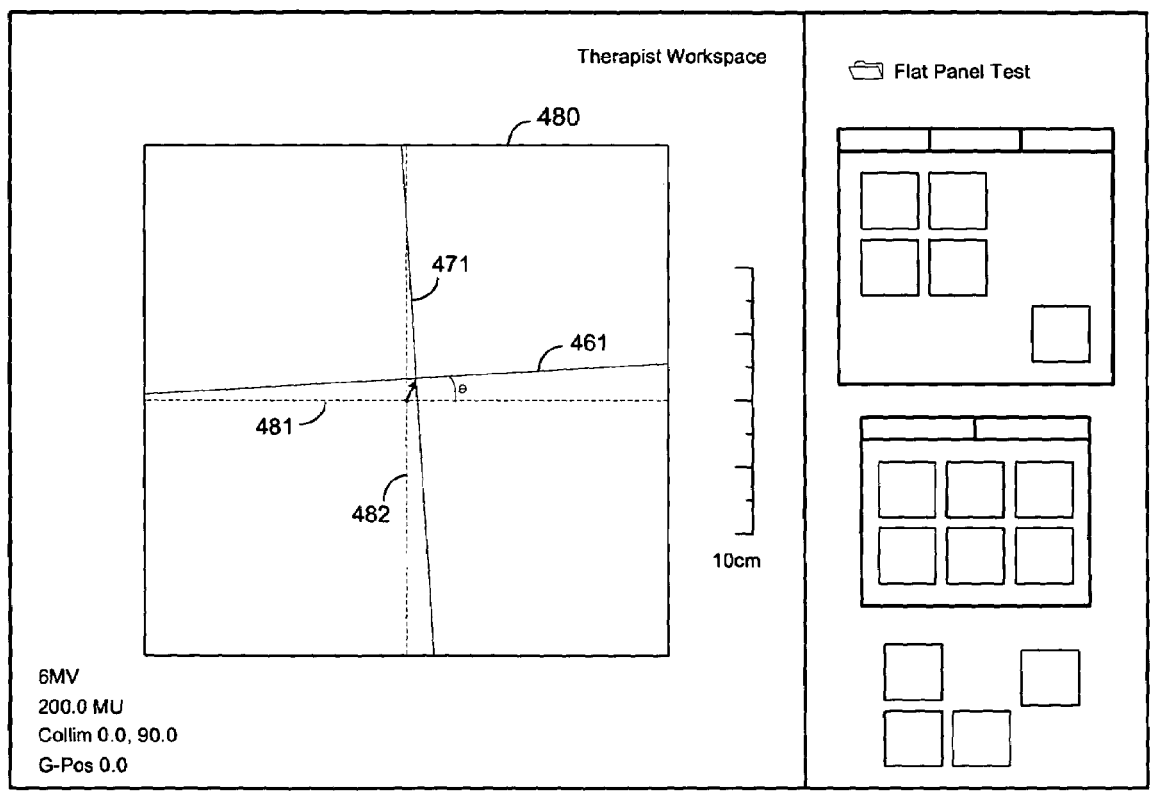
FIG. 11 is a view of a graphical interface of a linear accelerator system according to some embodiments.

An intersection point between the image of the radiation beam and the image of the second radiation beam is determined at step 405. FIG. 11 shows composite image 480 in which line 461 and line 471 are superimposed on one another. The intersection point may therefore be determined based on composite image 480. It will be assumed that Y-jaws 81 and 82 are aligned with axis 102 so as to uniformly rotate therearound. Accordingly, the intersection point of image 480 represents a point at which axis 102 intercepts imaging device 40.

Next, at step 406, a center of image of the first radiation beam or a center of image of the first radiation beam is determined. The determined center may correspond with the geometric center of images 460, 470 and/or 480, and might reflect a center of an image-capturing area of imaging device 40. The determined center is depicted in FIG. 11 as the intersection of dotted lines 481 and 482.

A vector between the center and the intersection point is determined at step 407. The vector represents the above-described first (translational) misalignment between axis 102 and a center of an image-capturing area of imaging device 40. The vector according to some embodiments is illustrated as an arrow in image 480 of FIG. 11. The vector may be represented by the coordinates of the determined intersection point, $(x_d, y_d)$.

At step 408, a portion of the image of the first radiation beam or of the image of the second radiation beam having a first orientation is determined. According to the present example, and as described above, line 461 is oriented along axis x and line 471 is oriented along axis y. Next, at step 409, an angle is determined between the determined portion and a line associated with the first orientation.

Such an angle is illustrated between line 461 and line 481 in FIG. 11. In this regard, line 481 is associated with an orientation along axis x because it is intended to be aligned therewith, even though it is not. Line 482 is associated with an orientation along axis y because it would be aligned therewith if imaging device 40 were correctly aligned with the radiation beam path. According to some embodiments, the angle between the determined portion and a line associated with the first orientation may be determined according to [(angle(line 461)–0°)+(angle(line 471)–90°)].

The determined vector and angle describe a translational misalignment of imaging device 40 as well as a rotational misalignment (i.e., yaw) of imaging device 40 in a plane defined by axis x and axis y. As mentioned above, the vector and angle may be used to modify images acquired by imaging device 40.

The translational misalignment represented by vector $(x_d, y_d)$ may be incorporated into the DICOM attribute X-Ray Image Receptor Translation, tag (3002,000D), in the following manner:

$X = \text{epidX} + x_d$ $Y = \text{epidY} + y_d$ $Z = \text{SAD} - \text{SID}$, where SAD=Source Axis Distance and SID=Source Imager Distance, and where epidX and epidY are the nominal IEC coordinates of the center of the flat panel (e.g., (0,0)).

Moreover, the rotational misalignment Θ may be used as the DICOM attribute X-Ray Image Receptor Angle, tag (3002,000E).

According to some embodiments, process steps 300 and/or process steps 400 are performed at various gantry rotational angles (e.g., 0°, 45°, 90°, etc.). In order to address gravitational and other effects, the determined vector and angle for a given gantry rotational angle may be used to modify images acquired at similar gantry rotational angles.

Figure 12:
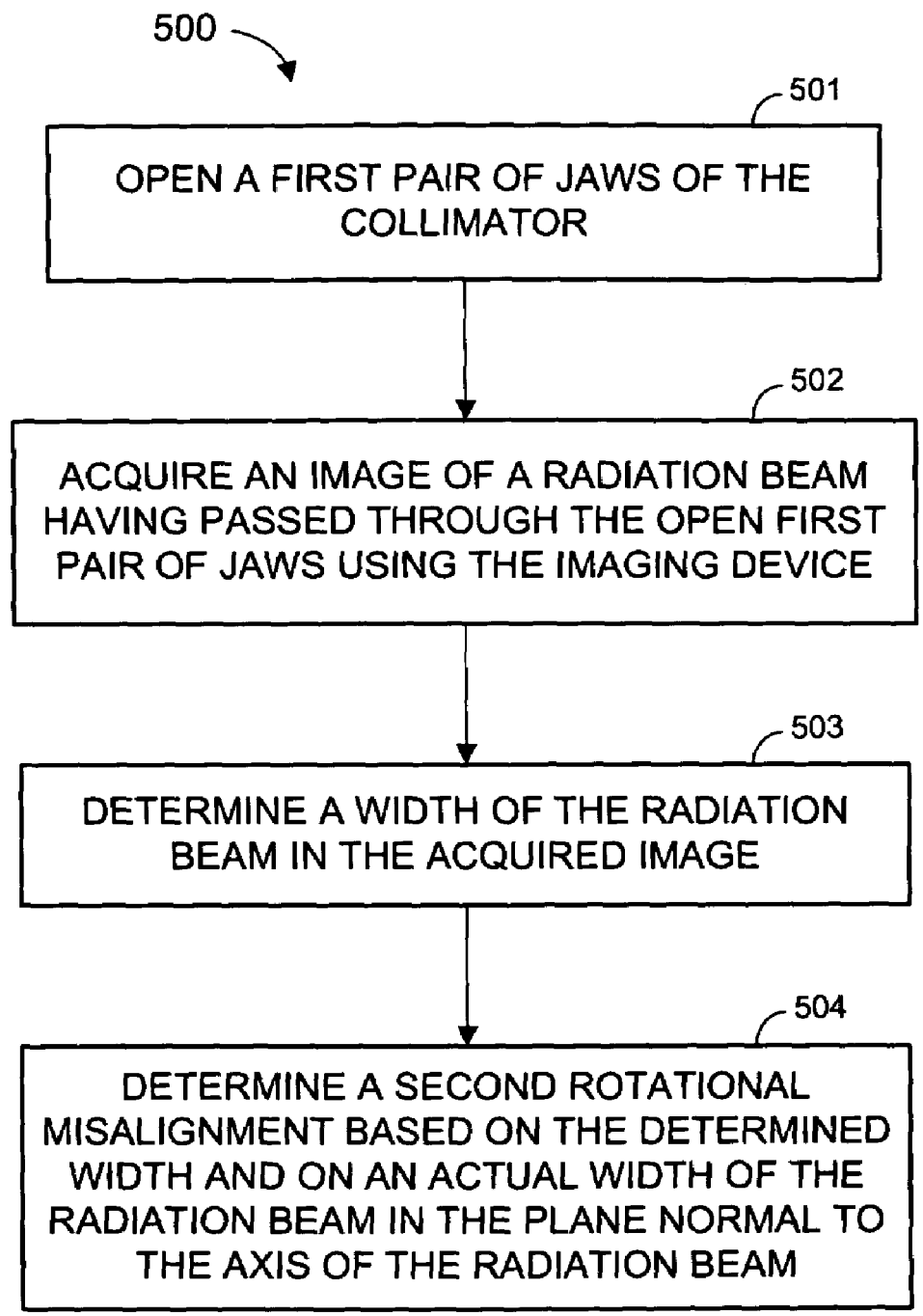
FIG. 12 is a flow diagram of process steps pursuant to some embodiments.
Figure 13:
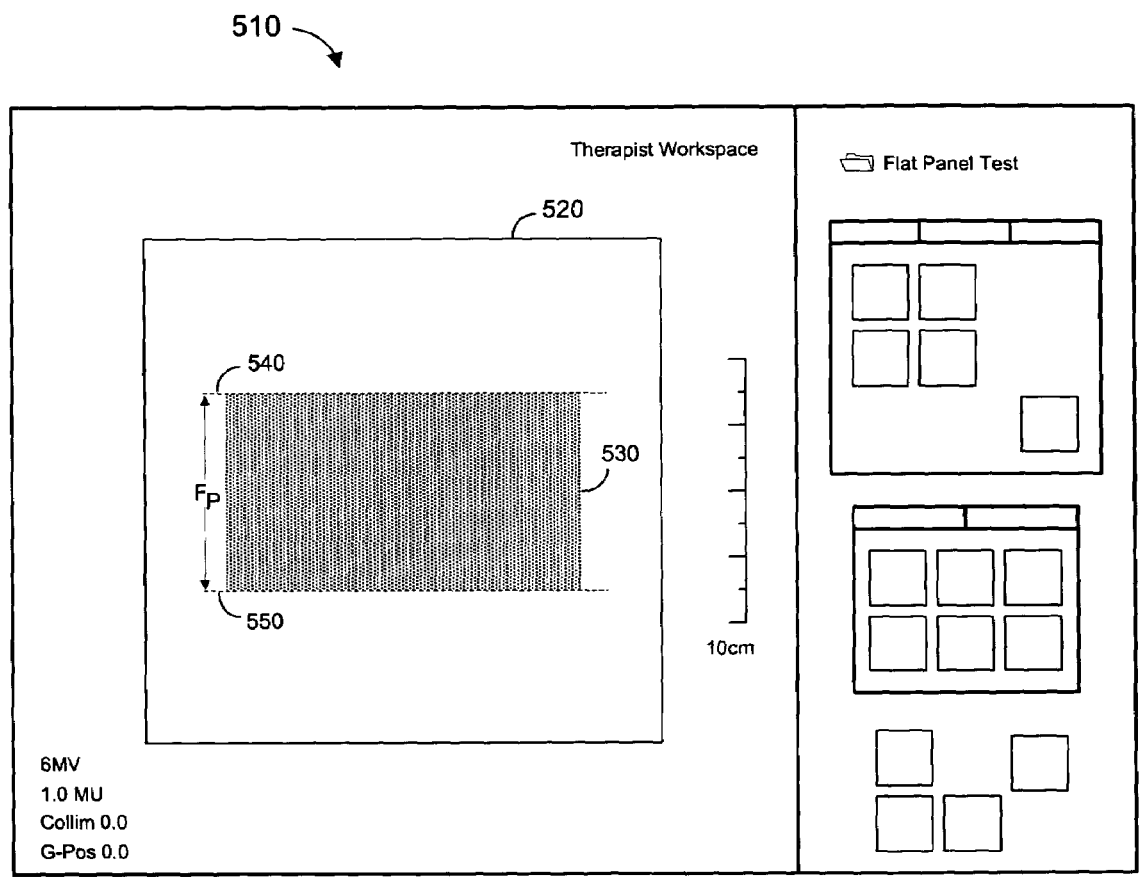
FIG. 13 is a view of a graphical interface of a linear accelerator system according to some embodiments.

Process steps 500 of FIG. 12 may be performed to determine a second rotational misalignment between an imaging device and a plane normal to the axis of a radiation beam according to some embodiments. Referring to FIG. 2, the plane may be defined by axis x and axis y, and the second rotational misalignment may consist of roll or pitch. An acquired image may therefore be modified at step 74 based on the determined first (translational) misalignment, rotational misalignment and second rotational misalignment.

At step 501, a first pair of jaws of a collimator is opened. According to some embodiments, Y-jaws 81 and 82 are opened to limit a radiation field at isocenter 60 to one 25 cm dimension, and X-jaws 83 and 84 are opened to limit the radiation field at isocenter 60 to one 30 cm dimension. Any other suitable dimensions may be used according to some embodiments.

An image of a radiation beam having passed through the opened first pair of jaws is acquired using an imaging device at step 502. FIG. 9 illustrates interface 510 presenting image 520 acquired according to some embodiments of step 502. Field 530 represents a radiation beam having passed through Y-jaws 81 and 82 as projected onto an image-capturing area of imaging device 40.

A width of the radiation beam in the acquired image is determined at step 503. The width in the present example corresponds to a dimension controlled by the opened Y-jaws 81 and 82. The width may be determined by determining boundary lines 540 and 550 and by calculating the distance therebetween. The width, $F_P$, is related to a pitch angle of imaging device 40 because the width is defined by Y-jaws 81 and 82 and collimator 80 is disposed in its home position.

A second rotational misalignment is determined at step 504 based on the determined width and on an actual width of the radiation beam in a plane normal to an axis of the radiation beam. The plane is defined by axis x and axis y according to the present example. The actual width of the radiation beam in the plane is determined based on the corresponding width in the plane of isocenter 60, the SID and the SAD. For example, $F_A$=300 mm if a corresponding field size $F_I$ at isocenter 60 is 250 mm, the SID=1200 mm, and the SAD=1000 mm.

Figure 14:
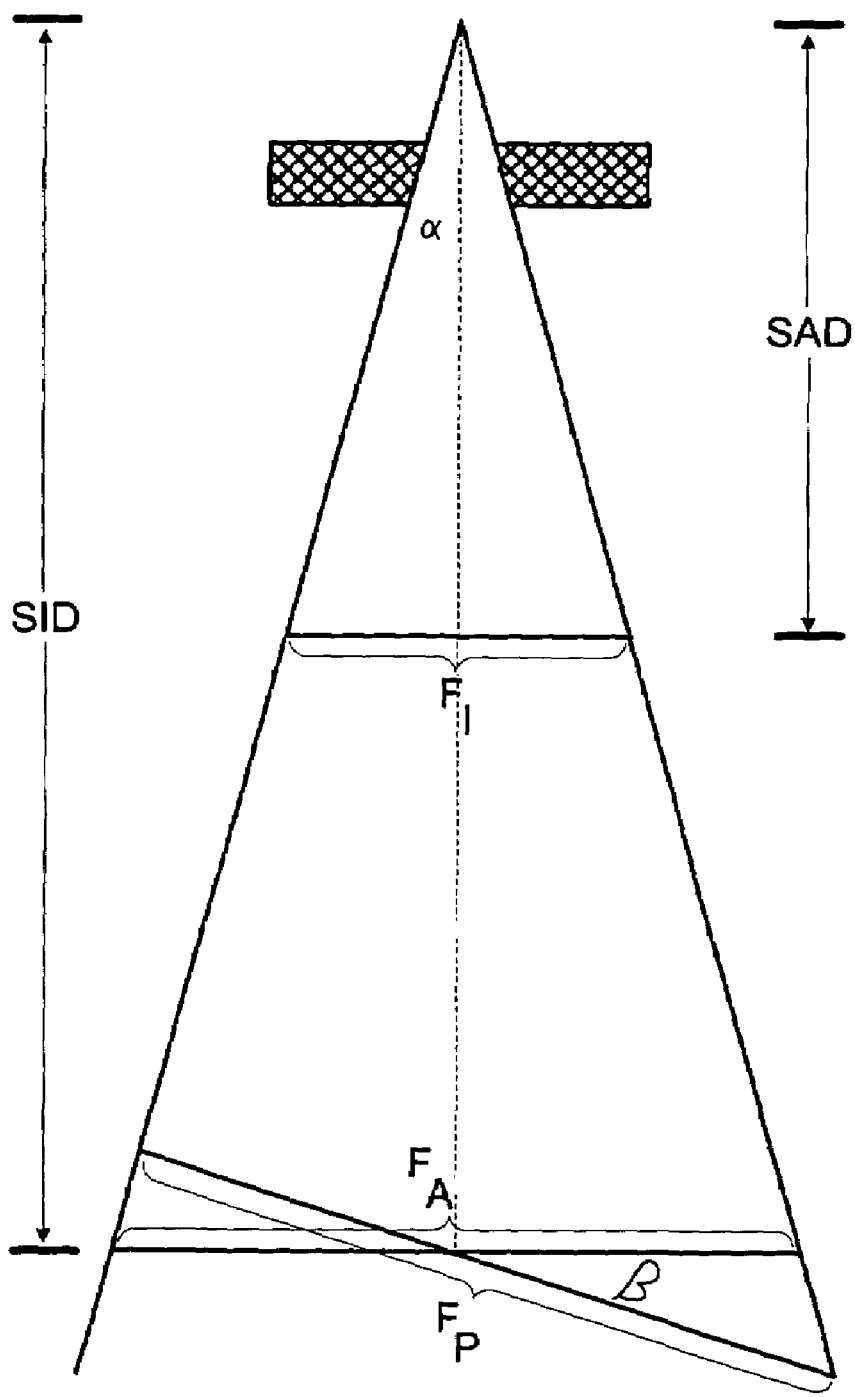
FIG. 14 is a diagram for illustrating a determination of rotational misalignment according to some embodiments.

FIG. 14 comprises a diagram illustrating the above-mentioned distances, wherein β represents a pitch angle describing the second rotational misalignment. β can therefore be determined at step 504 based on the illustrated geometric relationships and on the values for $F_P$ and $F_A$.

Figure 15:
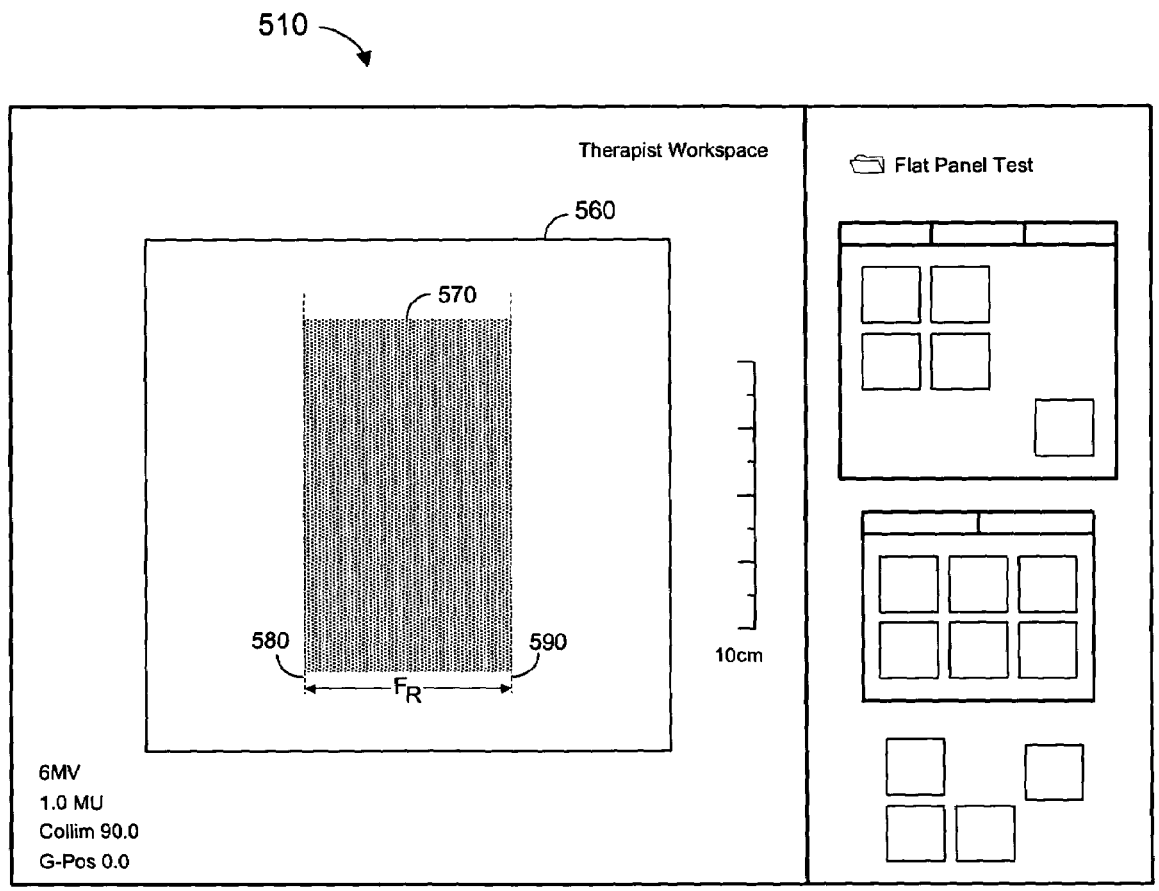
FIG. 15 is a view of a graphical interface of a linear accelerator system according to some embodiments.

Process steps 500 may also be used to determine a second rotational misalignment consisting of a roll angle. According to some embodiments, such a determination proceeds as described above but collimator 80 is rotated 90° from its home position prior to acquiring the image at 502. FIG. 15 illustrates image 560 that may be acquired during determination of a roll angle. Width $F_R$ is determined at step 503 based on boundary lines 580 and 590, and roll angle β is determined based on $F_R$ and $F_A$ and the relationships shown in FIG. 15.

Process steps 600 of FIG. 16 may also be performed to determine a second rotational misalignment between an imaging device and a plane normal to the axis of a radiation beam according to some embodiments. Again, the second rotational misalignment may consist of roll or pitch. An acquired image may be modified at step 74 based at least in part on this determined second rotational misalignment.

A first jaw of a first pair of jaws of a collimator is opened at step 601. According to some embodiments of step 601, Y-jaw 81 is left at its home position and Y-jaw 82 is partially opened. Such a configuration may result in a radiation field extending 12.5 cm in one direction (e.g., along axis x) from isocenter 60 and extending 0 cm in an opposite direction (still along axis x) from isocenter 60. X-jaws 83 and 84 may be fully opened to limit the radiation field at isocenter 60 to 30 cm in the direction of axis y. Any other suitable configurations and field dimensions may be used according to some embodiments of process steps 600.

Figure 17A:
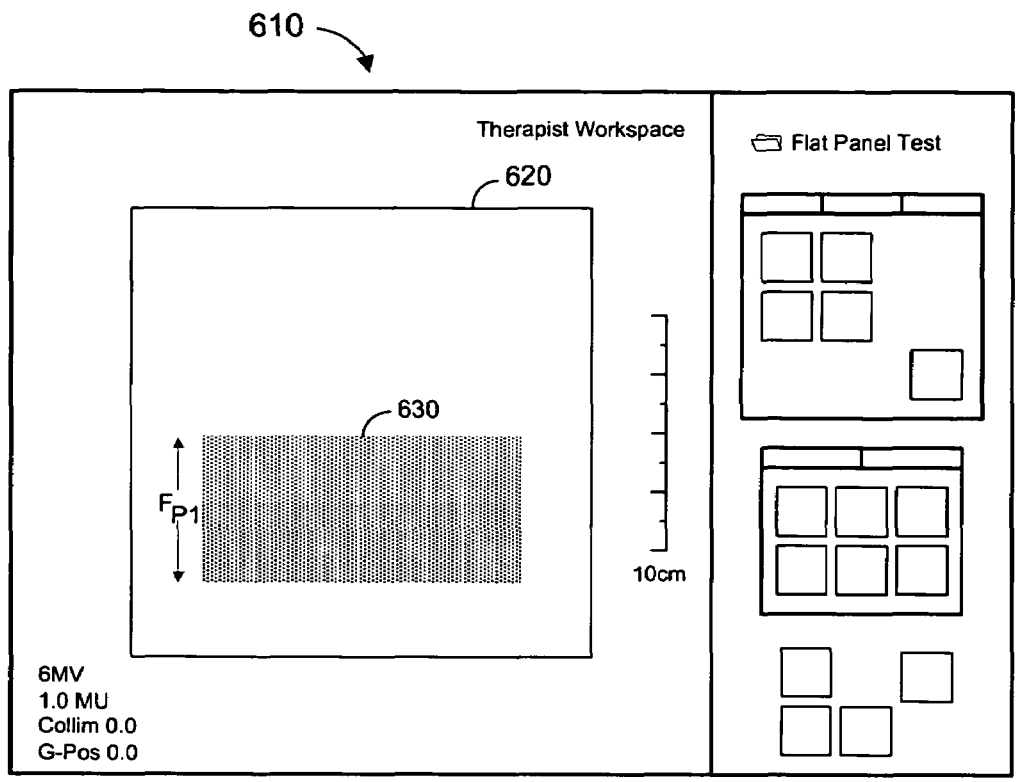
FIG. 17A is a view of a graphical interface of a linear accelerator system according to some embodiments.

An image of a radiation beam having passed through the first pair of jaws is acquired using an imaging device at step 602. FIG. 17A illustrates interface 610 and image 620 acquired according to some embodiments of step 602. Field 630 represents a radiation beam having passed through Y-jaws 81 and 82 as projected onto an image-capturing area of imaging device 40.

Next, a width of the radiation beam in the acquired image is determined at step 603. The width in the present example is determined along a dimension controlled by the opened Y-jaws 81 and 82. The width is illustrated as $F_{P1}$ in FIG. 17A. Width $F_{P1}$ is related to a pitch angle of imaging device 40 because the width is defined by Y-jaws 81 and 82 and because collimator 80 is disposed in its home position.

Figure 18A:
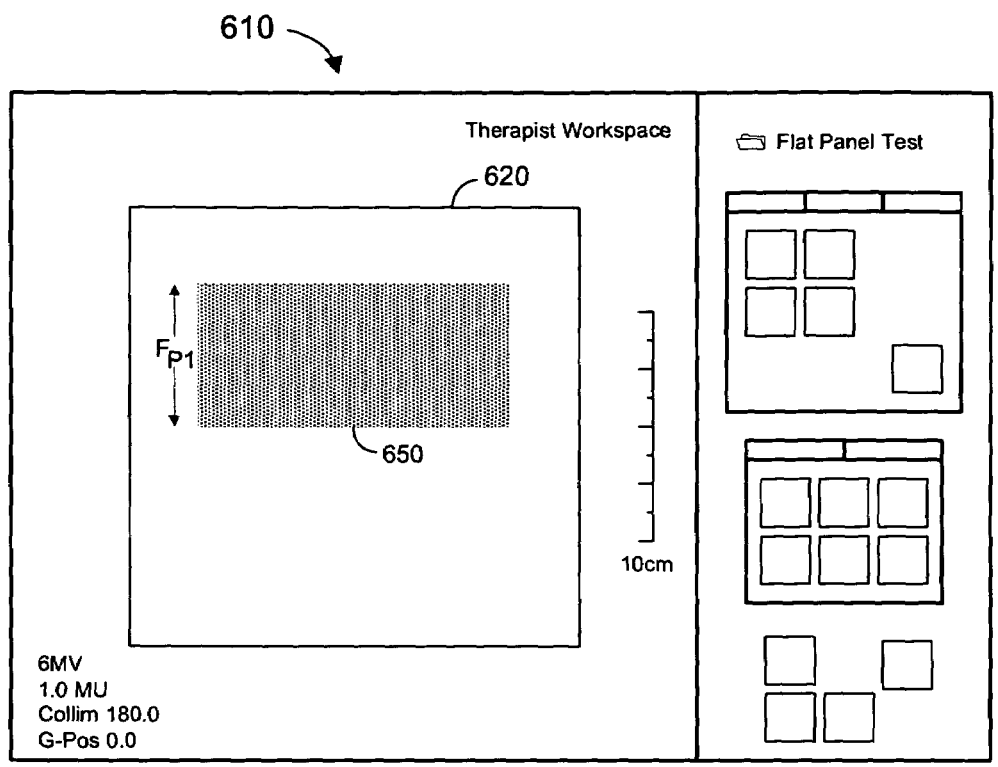
FIG. 18A is a view of a graphical interface of a linear accelerator system according to some embodiments.

The collimator is then rotated by 180° at step 604. This rotation causes Y-jaws 81 and 82 to exchange their respective positions around axis 102. An image of a second radiation beam having passed through the first pair of jaws is acquired using an imaging device at step 605. FIG. 18A illustrates interface 610 and image 640 acquired according to some embodiments of step 605. As shown, the rotation of collimator 80 produces field 650 extending in an opposite direction than that shown in FIG. 17A.

A width of the radiation beam in the second acquired image is determined at step 606. The width is illustrated as $F_{P2}$ in FIG. 18A. Width $F_{P2}$ is related to a pitch angle of imaging device 40 because width $F_{P2}$ is defined by Y-jaws 81 and 82 and because collimator 80 is disposed 180° from its home position.

A second rotational misalignment is determined at step 607 based on the determined widths and on an actual width F of the radiation beam in a plane normal to an axis of the radiation beam. As described above, the actual width F of the radiation beam in the plane may be determined based on the corresponding width of the radiation beam in the plane of isocenter 60, the SID and the SAD.

Figure 17B:
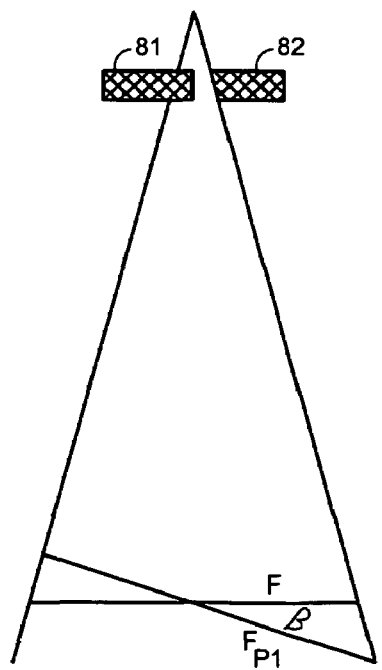
FIG. 17B is a diagram for illustrating a determination of rotational misalignment according to some embodiments.
Figure 18B:
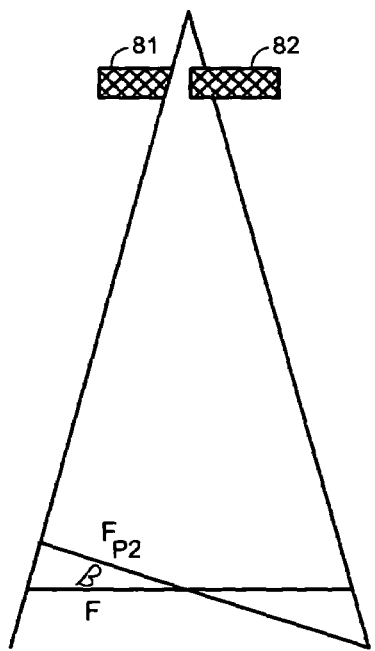
FIG. 18B is a diagram for illustrating a determination of rotational misalignment according to some embodiments.

According to some embodiments, β of FIGS. 17B and 18B represents a pitch angle representing the second rotational misalignment. If $F_{P1} > F_{P2}$, $\beta = \cos^{-1}(\cos(\alpha F/F_{P1}) - \alpha$, where $\alpha = \tan^{-1}(F/SID)$. If $F_{P1} < F_{P2}$, $-\beta = \cos^{-1}(\cos(\alpha F/F_{P2}) - \alpha$, where $\alpha = \tan^{-1}(F/SID)$.

Figure 19A:
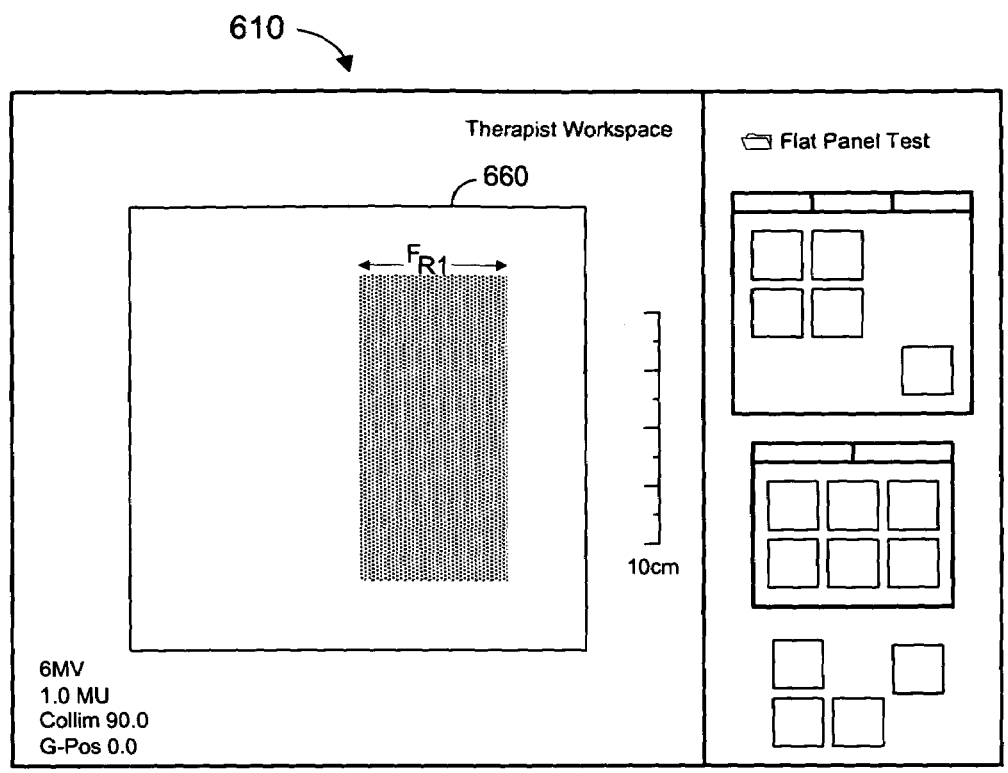
FIG. 19A is a view of a graphical interface of a linear accelerator system according to some embodiments.
Figure 20A:
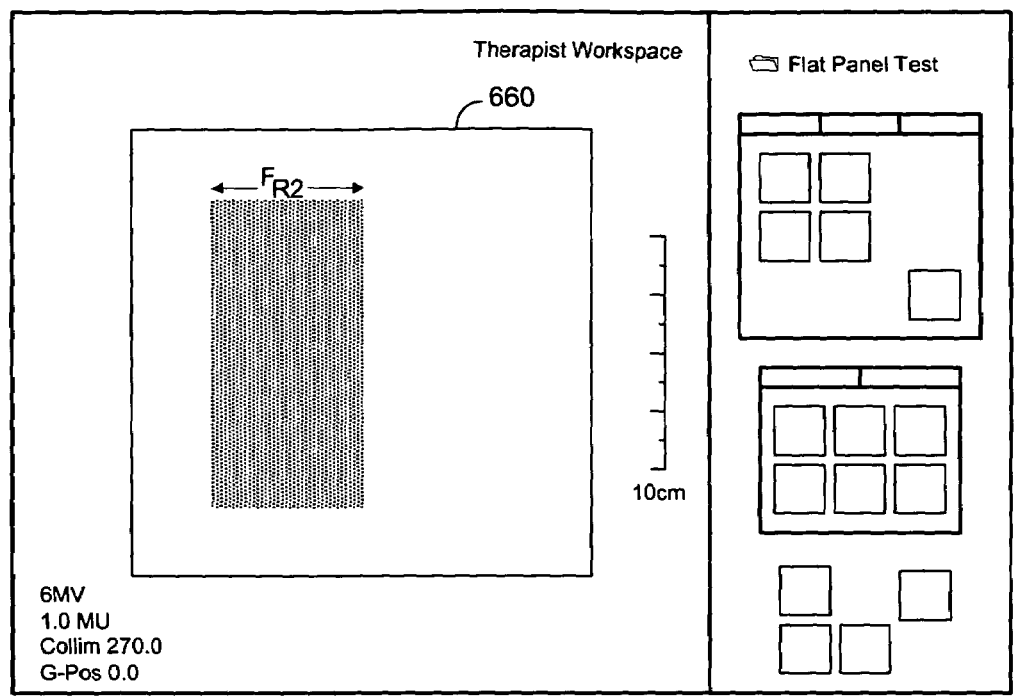
FIG. 20A is a view of a graphical interface of a linear accelerator system according to some embodiments.

Process steps 600 may also be used to determine a second rotational misalignment consisting of a roll angle. According to some embodiments, such a determination proceeds as described above but collimator 80 is rotated 90° from its home position prior to acquiring the image at 602. FIG. 19A illustrates resulting image 660 and width $F_{R1}$ determined at step 603. The second image is therefore acquired at step 605 with collimator 80 being rotated 270° from its home position. Resulting image 660 and its width $F_{R2}$ are shown in FIG. 20A.

Figure 19B:
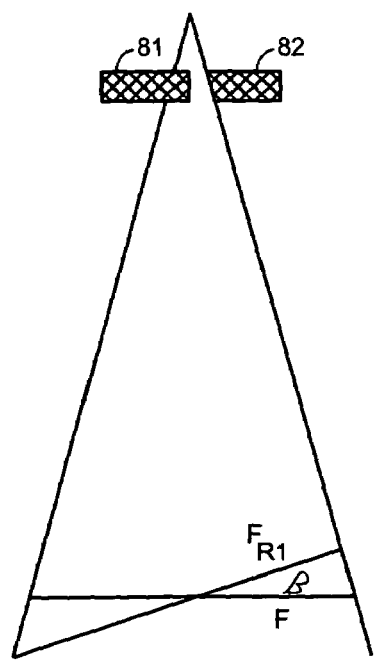
FIG. 19B is a diagram for illustrating a determination of rotational misalignment according to some embodiments.
Figure 20B:
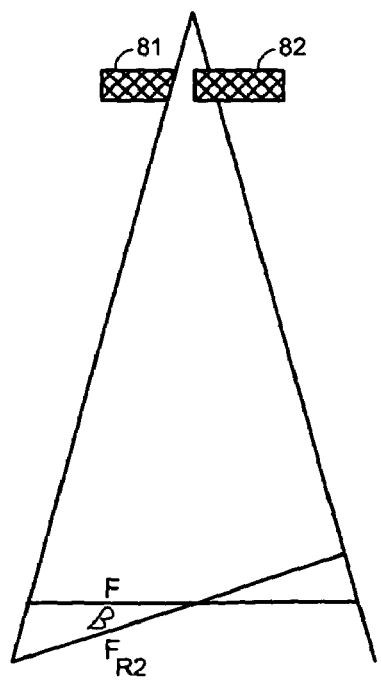
FIG. 20B is a diagram for illustrating a determination of rotational misalignment according to some embodiments.

The second rotational misalignment may thereafter be determined as roll angle β shown in of FIGS. 19B and 20B. More particularly, if $F_{R1} > F_{R2}$, $-\beta = \cos^{-1}(\cos(\alpha F/F_{P1}) - \alpha$, where $\alpha = \tan^{-1}(F/SID)$. If $F_{R1} < F_{R2}$, $\beta = \cos^{-1}(\cos(\alpha F/F_{P2}) - \alpha$, where $\alpha = \tan^{-1}(F/SID)$.

The determined pitch and/or roll angles may be used to adjust the physical alignment between an imaging device and a radiation beam path. The determined pitch and/or roll angles may be used to modify images that are subsequently acquired by the imaging device as described with respect to step 74 of process steps 70. In this regard, the determined pitch and/or roll angles may be incorporated into a future DICOM attribute to efficiently modify such subsequently-acquired images.

Some embodiments provide efficient mechanical adjustment and alignment of an imaging device with respect to a radiation beam. Such adjustment and alignment may be faster and/or more accurate than that provided by conventional systems. Any or all of the process steps herein may be used to provide quality control and/or automatic geometrical calibration.

The several embodiments described herein are solely for the purpose of illustration. Therefore, persons in the art will recognize from this description that other embodiments may be practiced with various modifications and alterations.

What is claimed is:

1. A method comprising:
   determining a first misalignment between an imaging device and an axis of a radiation beam emitted from a treatment head;
   determining a rotational misalignment between the imaging device and the radiation beam within a plane normal to the axis of the radiation beam;
   acquiring an image using the imaging device; and
   modifying the acquired image based on the determined first misalignment and rotational misalignment.

2. A method according to claim 1, wherein the image is acquired while the imaging device is at a first position and the treatment head is at a second position, the method further comprising:
   moving the imaging device to a third position and the treatment head to a fourth position;
   determining a second misalignment between the imaging device at the third position and a second axis of a second radiation beam emitted from the treatment head at the a fourth position;
   determining a second rotational misalignment between the imaging device at the third position and the second radiation beam within a plane normal to the axis of the radiation beam;
   acquiring a second image using the imaging device while the imaging device is at the third position and the treatment head is at the fourth position; and
   modifying the acquired second image based on the determined second misalignment and second rotational misalignment.

3. A method according to claim 1, wherein determining the first misalignment comprises:
   acquiring, using the imaging device, an image of a reticle mounted to the treatment head;
   determining a center of the reticle in the image;
   determining a center of the image; and
   determining a vector between the center of the image and the center of the reticle in the image.

4. A method according to claim 3, wherein determining the rotational misalignment comprises:
   determining a portion of the reticle in the image having a first orientation; and
   determining an angle between the portion and a line associated with the first orientation.

5. A method according to claim 1, wherein determining the first misalignment comprises:
   substantially closing a first pair of jaws of a collimator;
   acquiring, using the imaging device, an image of a radiation beam having passed through the substantially closed first pair of jaws;
   rotating the collimator;
   acquiring, using the imaging device, an image of a second radiation beam having passed through the substantially closed first pair of jaws;
   determining an intersection point between the image of the first radiation beam and the image of the second radiation beam;
   determining a center of the image of the first radiation beam or of the image of the second radiation beam; and
   determining a vector between the center and the intersection point.

6. A method according to claim 5, wherein determining the rotational misalignment comprises:
   determining a portion of the image of the first radiation beam having a first orientation; and
   determining an angle between the portion and a line associated with the first orientation.

7. A method according to claim 1, wherein determining the rotational misalignment comprises:
   acquiring, using the imaging device, an image of a reticle mounted to the treatment head;
   determining a portion of the reticle in the image having a first orientation; and
   determining an angle between the portion and a line associated with the first orientation.

8. A method according to claim 1, wherein determining the rotational misalignment comprises:
   substantially closing a first pair of jaws of a collimator;
   acquiring, using the imaging device, an image of a radiation beam having passed through the substantially closed first pair of jaws;
   determining a portion of the image of the first radiation beam having a first orientation; and
   determining an angle between the portion and a line associated with the first orientation.

9. A method according to claim 1, further comprising:
   determining a second rotational misalignment between the imaging device and the plane normal to the axis of the radiation beam,
   wherein modifying the acquired image comprises modifying the acquired image based on the determined first misalignment, rotational misalignment and second rotational misalignment.

10. A method according to claim 9, wherein determining the second rotational misalignment comprises:
    opening a first pair of jaws of a collimator;
    acquiring, using the imaging device, an image of a radiation beam having passed through the first pair of jaws;
    determining a width of the radiation beam in the acquired image; and
    determining the second rotational misalignment based on the width and on a width of the radiation beam in the plane normal to the axis of the radiation beam.

11. A method according to claim 10, wherein opening the first pair of jaws of the collimator comprises:
    opening a first jaw of the first pair of jaws,
    the method further comprising:
    rotating the collimator one hundred eighty degrees; and
    acquiring, using the imaging device, a second image of a second radiation beam having passed through the first pair of jaws with the collimator rotated one hundred eighty degrees; and determining a width of the second radiation beam in the second acquired image,
wherein determining the second rotational misalignment comprises determining the second rotational misalignment based on the width of the radiation beam, the width of the second radiation beam, and on the width of the radiation beam in the plane normal to the axis of the radiation beam.

12. An apparatus comprising:
a treatment head to emit a radiation beam;
an imaging device to acquire an image based on the radiation beam; and
a processing device to:
  determine a first misalignment between the imaging device and an axis of the radiation beam;
  determine a rotational misalignment between the imaging device and the treatment head within a plane normal to the axis of the radiation beam; and
  modify the acquired image based on the determined first misalignment and rotational misalignment.

13. An apparatus according to claim 12, wherein the image is acquired while the imaging device is at a first position and the treatment head is at a second position, and wherein the processing device is to:
  move the imaging device to a third position and the treatment head to a fourth position;
  determine a second misalignment between the imaging device at the third position and a second axis of a second radiation beam emitted from the treatment head at the a fourth position;
  determine a second rotational misalignment between the imaging device at the third position and the second radiation beam within a plane normal to the axis of the radiation beam;
  acquire a second image using the imaging device while the imaging device is at the third position and the treatment head is at the fourth position; and
  modify the acquired second image based on the determined second misalignment and second rotational misalignment.

14. An apparatus according to claim 12, wherein determination of the first misalignment comprises:
  acquisition, using the imaging device, an image of a reticle mounted to the treatment head;
  determination of a center of the reticle in the image;
  determination of a center of the image; and
  determination of a vector between the center of the image and the center of the reticle in the image.

15. An apparatus according to claim 14, wherein determination of the rotational misalignment comprises:
  determination of a portion of the reticle in the image having a first orientation; and
  determination of an angle between the portion and a line associated with the first orientation.

16. An apparatus according to claim 12, further comprising:
  a collimator mounted to the treatment head, the collimator comprising at least a first pair of jaws,
  wherein determination of the first misalignment comprises:
    substantial closing of the first pair of jaws;
    acquisition, using the imaging device, of an image of a radiation beam having passed through the substantially closed first pair of jaws;
    rotation of the collimator;
    acquisition, using the imaging device, of an image of a second radiation beam having passed through the substantially closed first pair of jaws;
    determination of an intersection point between the image of the first radiation beam and the image of the second radiation beam;
    determination of a center of the image of the first radiation beam or of the image of the second radiation beam; and
    determination of a vector between the center and the intersection point.

17. An apparatus according to claim 16, wherein determination of the rotational misalignment comprises:
  determination of a portion of the image of the first radiation beam having a first orientation; and
  determination of an angle between the portion and a line associated with the first orientation.

18. An apparatus according to claim 12, wherein determination of the rotational misalignment comprises:
  acquisition of, using the imaging device, an image of a reticle mounted to the treatment head;
  determination of a portion of the reticle in the image having a first orientation; and
  determination of an angle between the portion and a line associated with the first orientation.

19. An apparatus according to claim 12, further comprising:
  a collimator mounted to the treatment head, the collimator comprising at least a first pair of jaws,
  wherein determination of the rotational misalignment comprises:
    substantial closing of the first pair of jaws;
    acquisition, using the imaging device, of an image of a radiation beam having passed through the substantially closed first pair of jaws;
    determination of a portion of the image of the first radiation beam having a first orientation; and
    determination of an angle between the portion and a line associated with the first orientation.

20. An apparatus according to claim 12, wherein the processing device is to determine a second rotational misalignment between the imaging device and the plane normal to the axis of the radiation beam, and
  wherein modification of the acquired image comprises modification of the acquired image based on the determined first misalignment, rotational misalignment and second rotational misalignment.

21. An apparatus according to claim 20, further comprising:
  a collimator mounted to the treatment head, the collimator comprising at least a first pair of jaws,
  wherein, to determine the second rotational misalignment, the processing device is to:
    open the first pair of jaws;
    acquire, using the imaging device, an image of a radiation beam having passed through the open first pair of jaws;
    determine a width of the radiation beam in the acquired image; and
    determine the second rotational misalignment based on the width and on a width of the radiation beam in the plane normal to the axis of the radiation beam.

22. An apparatus according to claim 21, wherein opening of the first pair of jaws comprises:
  opening of a first jaw of the first pair of jaws; and
  wherein the processing device is to:
    rotate the collimator one hundred eighty degrees; and acquire, using the imaging device, a second image of a second radiation beam having passed through the first pair of jaws with the collimator rotated one hundred eighty degrees;

determine a width of the second radiation beam in the second acquired image; and determine the second rotational misalignment based on the width of the radiation beam, the width of the second radiation beam, and on a width of the radiation beam in the plane normal to the axis of the radiation beam.

23. A medium storing program code, the program code comprising:

code to determine a first misalignment between an imaging device and an axis of a radiation beam emitted from a treatment head;

code to determine a rotational misalignment between the imaging device and the treatment head within a plane normal to the axis of the radiation beam;

code to acquire an image using the imaging device; and code to modify the acquired image based on the determined first misalignment and rotational misalignment.

24. A medium according to claim 23, wherein the code to acquire the image comprises code to acquire the image while the imaging device is at a first position and the treatment head is at a second position, and the program code further comprising:

code to move the imaging device to a third position and the treatment head to a fourth position;

code to determine a second misalignment between the imaging device at the third position and a second axis of a second radiation beam emitted from the treatment head at the a fourth position;

code to determine a second rotational misalignment between the imaging device at the third position and the second radiation beam within a plane normal to the axis of the radiation beam;

code to acquire a second image using the imaging device while the imaging device is at the third position and the treatment head is at the fourth position; and code to modify the acquired second image based on the determined second misalignment and second rotational misalignment.

25. A medium according to claim 23, wherein the code to determine the first misalignment comprises:

code to acquire, using the imaging device, an image of a reticle mounted to the treatment head;

code to determine a center of the reticle in the image;

code to determine a center of the image; and code to determine a vector between the center of the image and the center of the reticle in the image.

26. A medium according to claim 25, wherein the code to determine the rotational misalignment comprises:

code to determine a portion of the reticle in the image having a first orientation; and code to determine an angle between the portion and a line associated with the first orientation.

27. A medium according to claim 23, wherein the code to determine the first misalignment comprises:

code to substantially close a first pair of jaws of a collimator;

code to acquire, using the imaging device, an image of a radiation beam having passed through the substantially closed first pair of jaws;

code to rotate the collimator;

code to acquire, using the imaging device, an image of a second radiation beam having passed through the substantially closed first pair of jaws;

code to determine an intersection point between the image of the first radiation beam and the image of the second radiation beam;

code to determine a center of the image of the first radiation beam or of the image of the second radiation beam; and code to determine a vector between the center of the image and the intersection point.

28. A medium according to claim 23, the program code further comprising:

code to determine a second rotational misalignment between the imaging device and the plane normal to the axis of the radiation beam, wherein the code to modify the acquired image comprises code to modify the acquired image based on the determined first misalignment, rotational misalignment and second rotational misalignment.

29. A medium according to claim 28, wherein the code to determine the second rotational misalignment comprises:

code to open a first pair of jaws of a collimator;

code to acquire, using the imaging device, an image of a radiation beam having passed through the first pair of jaws;

code to determine a width of the radiation beam in the acquired image; and code to determine the second rotational misalignment based on the width and on a width of the radiation beam in the plane normal to the axis of the radiation beam.

30. A medium according to claim 29, wherein the code to open the first pair of jaws of the collimator comprises:

code to open a first jaw of the first pair of jaws, the program code further comprising:

code to rotate the collimator one hundred eighty degrees; and code to acquire, using the imaging device, a second image of a second radiation beam having passed through the first pair of jaws with the collimator rotated one hundred eighty degrees; and code to determine a width of the second radiation beam in the second acquired image, wherein the code to determine the second rotational misalignment comprises code to determine the second rotational misalignment based on the width of the radiation beam, the width of the second radiation beam, and on a width of the radiation beam field in the plane normal to the axis of the radiation beam.

* * * * *